United States Patent
Pili

(10) Patent No.: US 10,813,919 B2
(45) Date of Patent: Oct. 27, 2020

(54) USE OF HISTONE DEACETYLASE INHIBITORS FOR ENHANCING IMMUNOTHERAPIES

(71) Applicant: Indiana University Research and Technology Corporation, Indianapolis, IN (US)

(72) Inventor: Roberto Pili, Carmel, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 8 days.

(21) Appl. No.: 16/072,659

(22) PCT Filed: Jan. 27, 2017

(86) PCT No.: PCT/US2017/015389
§ 371 (c)(1),
(2) Date: Jul. 25, 2018

(87) PCT Pub. No.: WO2017/132536
PCT Pub. Date: Aug. 3, 2017

(65) Prior Publication Data
US 2019/0030011 A1   Jan. 31, 2019

Related U.S. Application Data

(60) Provisional application No. 62/288,121, filed on Jan. 28, 2016.

(51) Int. Cl.
| | | |
|---|---|---|
| *A61K 31/4406* | (2006.01) | |
| *A61K 45/06* | (2006.01) | |
| *A61P 37/02* | (2006.01) | |
| *A61P 35/00* | (2006.01) | |
| *A61K 39/395* | (2006.01) | |
| *C07K 16/28* | (2006.01) | |
| *A61K 39/00* | (2006.01) | |

(52) U.S. Cl.
CPC .... *A61K 31/4406* (2013.01); *A61K 39/39558* (2013.01); *A61K 45/06* (2013.01); *A61P 35/00* (2018.01); *A61P 37/02* (2018.01); *C07K 16/2818* (2013.01); *A61K 2039/505* (2013.01); *A61K 2300/00* (2013.01)

(58) Field of Classification Search
CPC .......... A61K 31/406; A61K 39/39558; A61K 45/06; A61P 37/02; A61P 35/00; C07K 16/2818
USPC ......................................................... 514/250
See application file for complete search history.

(56) References Cited

FOREIGN PATENT DOCUMENTS

| | | |
|---|---|---|
| WO | 2008083174 A2 | 7/2008 |
| WO | 2015157162 A1 | 10/2015 |
| WO | 2016154068 A1 | 9/2016 |
| WO | 2017035453 A1 | 3/2017 |
| WO | 2017041043 A1 | 3/2017 |

OTHER PUBLICATIONS

Gangadhar et al., Clinical applications of PD-1-based therapy: a focus on pembrolizumab (MK-3475) in the management of melanoma and other tumor types; Onco Targcs and Therapy, 2015; vol. 8, pp. 929-937.

Kato et al., Synergistic In vivo Antitumor Effect of the Histone Deacetylase Inhibitor MS-275 in Combination with Interleukin 2 in a Murine Model of Renal Cell Carcinoma; Cancer Therapy: Preclinical; Clin Cancer Res, 2007, vol. 13, No. 15, pp. 4538-4546.

Motzer et al., Nivolumab for Metastatic Renal Cell Carcinoma: Results of a Randomized Phase II Trial; Journal of Clinical Oncology; 2015, vol. 33, No. 13, pp. 1430-1443.

Pili et al., Class 1 histone deacetylase inhibition is a novel mechanism to target regulatory T cells in immunotherapy; OncoImmunology; 2016, vol. 1, No. 6, pp. 948-950.

Shen et al., Class 1 Histone Deacetylase Inhibitor Entinostat Suppresses Regulatory T Cells and Enhances Immunotherapies in Renal and Prostate Cancer Models; PLOS ONE; 2012, vol. 7, No. 1, p. e30815.

*Primary Examiner* — Yevgeny Valenrod
(74) *Attorney, Agent, or Firm* — Stinson LLP

(57) ABSTRACT

Compositions including combinations of class I histone deacetylase (HDAC) inhibitors and programmed cell death protein 1 (PD-1) inhibitors for enhancing antitumor activity are disclosed. Further disclosed are methods of administering these compositions as immunotherapies for suppressing regulatory T cells in renal cell carcinoma.

20 Claims, 21 Drawing Sheets
Specification includes a Sequence Listing.

ial description thereof. Such detailed description
USE OF HISTONE DEACETYLASE INHIBITORS FOR ENHANCING IMMUNOTHERAPIES

CROSS REFERENCE TO RELATED APPLICATIONS

This application claims priority to International Publication Number WO 2017/132536, filed on Jan. 27, 2017, which claims priority to U.S. Provisional Application No. 62/288,121 filed Jan. 28, 2016, both of which are hereby incorporated by reference in their entireties.

STATEMENT IN SUPPORT FOR FILING A SEQUENCE LISTING

A computer readable form of the Sequence Listing containing the file named "IURTC_2016-086-02_ST25.txt", which is 878 bytes in size (as measured in MICROSOFT WINDOWS EXPLORER), is provided herein and is herein incorporated by reference. This Sequence Listing consists of SEQ ID NOs:1-3.

BACKGROUND OF THE DISCLOSURE

The present disclosure relates generally to compositions including combinations of class I histone deacetylase (HDAC) inhibitors and programmed cell death protein 1 (PD-1) inhibitors. Further, the use of these compositions for suppressing regulatory T cells and enhancing immunotherapies in renal cell carcinoma are disclosed.

During the last decade, immunotherapy has become one of the most attractive and extensively studied approaches for the treatment of solid tumors. However, current clinical studies of cancer immunotherapy still show very limited efficacy. Immune tolerance to cancer has been shown to be a major barrier. Tumor growth and stromal establishment modulate not only the local microenvironment but also peripheral components of the immune system to induce multiple levels of tolerance mechanisms: immunosuppressive cells such as regulatory T cells (Tregs), myeloid derived suppressor cells and tumor-associated macrophages; immunological checkpoints; and abnormal levels of circulating cytokines. Among these immunosuppressive factors, Tregs have been identified as one of the major players. The number or function of Tregs is usually promoted in cancer patients. Preclinical data also suggest the role of Tregs in inducing tolerance for tumor associated antigens. More importantly, immunotherapies such as cytokines and vaccines themselves may induce promotion of Treg number or function in the patient. Taken together, there is strong evidence that targeting Tregs can improve the efficacy of immunotherapy.

Most current strategies to target Tregs aim at depletion of Tregs with monoclonal antibodies or ligand-directed toxins that bind to the cell-surface receptor, CD25, or with metronomic cyclophosphamide treatment. These depletion approaches have limited clinical benefit, probably due to their side effect to eliminate activated T effector cells (Teffs) and induction of Tregs replenishment. Strategies targeting other surface markers also have specificity problems. More methods have been tested in animals to affect Treg intracellular protein expression, function or signaling, such as siRNA and miRNA approaches, which usually have restrictions and an important gap toward possible clinical applications.

Additionally, recent advances in treatment of patients with renal cell cancer (RCC) have opened doors for use of immune checkpoint inhibitors, such as nivolumab, a PD-1 inhibitor. The PD-1/PD-L1 axis plays a central role in the immune evasion capability of tumors by acting to diminish the antitumor activity of cytotoxic T cells. Blocking this immune checkpoint, which has been reported as aberrantly expressed in RCC, has recently shown promise yielding objective responses in 30-40% of ccRCC patients. Phase III clinical trial results have led to the approval of nivolumab by showing an unmistakable benefit from anti-PD-1 treatment in patients with advanced renal cell carcinoma. As compared to the standard of care, everolimus, nivolumab patients showed a 78% increase in overall survival with limited treatment related adverse events. However, despite these impressive clinical advances, immunotherapies for RCC and many other solid tumors are only a benefit to a subset of patients. Tumor escape from immune surveillance remains a major obstacle in effectively treating tumors from patients with RCC Based on the foregoing, there is a need in the art to develop alternative immunotherapies capable of targeting the suppression of Tregs such that the above limitations can be overcome.

BRIEF DESCRIPTION OF THE DISCLOSURE

The present disclosure is generally related to compositions including class I histone deacetylase (HDAC) inhibitors and programmed cell death protein 1 (PD-1) inhibitors for suppressing regulatory T cells (Treg) and enhancing immunotherapies in renal cell carcinoma. Particularly, in one embodiment, it has been found that the class I HDAC inhibitor, entinostat, enhances the antitumor effect of PD-1 inhibition.

In one aspect, the present disclosure is directed to a composition comprising a class I histone deacetylase (HDAC) inhibitor and a programmed cell death protein 1 (PD-1) inhibitor.

In another aspect, the present disclosure is directed to a method of suppressing regulatory T cells in an individual in need. The method comprises administering a composition comprising a class I histone deacetylase (HDAC) inhibitor and a programmed cell death protein 1 (PD-1) inhibitor to the individual.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

(FIG. 1A) Experimental time line, female Balb/c mice were injected orthotopically with $1\times10^4$ RENCA-Luc cells at day −8. Weekly bioluminescent imaging began at one week post-implantation and continued for the duration of Example 2. Treatment began on Day 1 of Example 2. (FIG. 1B) Top: baseline bioluminescent imaging. Bottom: endpoint bioluminescent imaging. Taken together these images show the inhibition of tumor growth in vivo. (FIG. 1C) Average Radiance [$p/s/cm^2/sr$] of each mouse in control, entinostat, anti-PD-1, and entinostat+anti-PD-1 cohorts across the duration of Example 2. (FIG. 1D) Images of end-point tumors for each group. Experiment 1 & 2 were performed sequentially to verify results. (FIG. 1E) End-point tumor weight in grams showing a significant reduction in tumor size with entinostat+anti-PD-1 immunotherapy (FIG. 1F) Left: Survival study, with 10 mg/kg of anti-PD-1, shows a significant shift in the survival curve of mice treated with entinostat+anti-PD-1 compared to the control and anti-PD-1 immunotherapy alone. Right: Survival study, with 20 mg/kg of anti-PD-1, shows a further significant shift in entinostat+anti-PD-1 compared to the control and entinostat cohorts, additionally, the increased dosage of anti-PD-1 immunotherapy prolonged mouse survival. Results are shown as mean±SEM (*p<0.05; p<0.01; *p<0.001; ****p<0.0001), tumor weight statistics were calculated using unpaired t test with Welch's correction; survival statistics calculated using Logrank (Mantel-Cox) test.

(FIG. 2A) Left: FACS analysis of blood shows the effect of vehicle and combination treatment on CD4 and FoxP3 levels. Right: Quantification of T regulatory cell presence in the blood and protein expression shown as mean fluorescence intensity (MFI) showing a significant increase in the presence of regulatory T cells with a decrease in FoxP3 in the combination cohort as compared to the control, functional transcription factor for T regulatory cells. (FIG. 2B) Left: FACS analysis of tumor-cell suspensions from RENCA mice after control or entinostat treatment. Right: Quantification of T regulatory cell presence in the TME and protein expression shown as mean fluorescence intensity (MFI) showing a slight increase in the presence of regulatory T cells in the combination cohort compared to the control with a significant decrease in FoxP3, functional transcription factor for T regulatory cells.

(FIG. 3A) Right: FACS analysis of tumor-cell suspensions from RENCA tumors after treatment with entinostat, anti-PD-1 immunotherapy, or combination. Left: Quantitative analysis of monocytic and granulocytic MDSC infiltrates into the TME represented as the percentage of Ly6C$^+$ and Ly6G$^+$ cells in the total population of CD45$^+$CD11b$^+$ cells showing a significant increase in the presence of both M-MDSCs and G-MDSCs in the combination cohort as compared to the control (n=3-5 tumors). (FIG. 3B) Quantitative FACS analysis of G-MDSC and M-MDSC presence in the blood showing a significant decrease in combination compared to control of G-MDSCs and a significant increase in M-MDSCs in the combination compared to the control (n=3-5 blood samples). (FIGS. 3C & 3D) G-MDSC and M-MDSC cells isolated from the TME were co-cultured with CFSE tagged CD8$^+$ T cells for 16-18 hours, at which time they were collected, stained with CD8 & Granzyme B antibodies, and subjected to FACS analysis for T cell proliferation. Results indicate a significant impairment of M-MDSC suppressive capacity when treated with entinostat in vivo (n=3-5 tumors) (FIG. 3C). Cells were harvested and co-cultured as described previously, results reveal a significant inhibition of G-MDSC suppressive capacity when treated with entinostat in vivo (n=3-5 tumors) (FIG. 3D). (FIG. 3E) FACS analysis of cytotoxic CD8$^+$ active protein Granzyme B from T cells which have been co-cultured with MDSCs from control, entinostat, or combination treated cohorts. (FIG. 3F) Quantitative representation of FACS analysis shows that MDSCs from entinostat and combination treated mice had less inhibitory capabilities of CD8$^+$ T cell activation via Granzyme B than the control. Results are shown as mean±SEM (*p<0.05; p<0.01; *p<0.001; ****p<0.0001), statistics were calculated using unpaired t test with Welch's correction.

(FIG. 4A) Characteristic FACS analysis of J774M cell line revealed that among the CD45$^+$CD11b$^+$Gr1$^+$ cells, approximately 90% of the cells are Ly6G$^+$ G-MDSC-like and 10% are Ly6C$^+$ M-MDSC-like cells, representative of what is typically seen in the TME. J774M cells were treated in vitro with entinostat for 24 hours, followed by co-culture with pre-activated CD8$^+$ T cells for 68-72 hours (FIG. 4B) Representative images of T cells at 68-72 hours of co-culture (scale bar: 400 μm). (FIG. 4C) CFSE fluorescent histograms of gated CD8$^+$ T cells incubated with J77M cells at a ratio of 1:1. J774M cells were treated with increasing concentrations of entinostat—from right to left: control (untreated), 0.01 μM, 0.05 μM, 0.25 μM, 0.37 μM, 0.5 μM. (FIG. 4D) Quantitative representation of FIG. 4B; bars show the mean percentage of proliferating CD8$^+$ T cells (n=3 technical replicates). This experiment was repeated 3 times independently. (FIG. 4E) Quantitative RT-PCR analysis indicates a significant decrease in key MDSC functional regulator Arginase-1 when J774M cells are treated with entinostat.

(FIG. 5A) Mouse cytokine/chemokine array results from tumor lysates in the control and entinostat treated cohorts (n=2 tumors/cohort & 3 data points per tumor). Tumor microenvironment analysis yielded significant alterations of a tumor suppressive environment. (FIG. 5B) Quantification of MDSC associated or pro-tumor cytokines/chemokines which were significantly downregulated in the presence of entinostat. (FIG. 5C) Quantification of anti-tumor chemokines/cytokines, which were upregulated significantly in the presence of entinostat treatment. (FIG. 5D) Left: Ary028 array results from serum samples of control and entinostat treated mice (n=2 tumors/cohort & 3 data points per tumor). Entinostat treatment alone inhibited many of the MDSC associated and pro-tumor cytokines and chemokines in circulation as is shown in the right panel of FIG. 5D. (FIG. 5E) Left: Array results comparing the control cohort with the combination cohort (n=2 tumors/cohort & 3 data points per tumor). Combination treatment significantly upregulated multiple anti-tumor associated chemokines and cytokines as shown in the right panel of FIG. 5E. Results are shown as mean±SEM (*p<0.05; p<0.01; *p<0.001; ****p<0.0001), statistics were calculated using multiple t tests, discovery was determined using the Two-stage linear step-up procedure of Benjamini, Krieger and Yekutieli, with Q=1%.

DETAILED DESCRIPTION

Figure 1A:
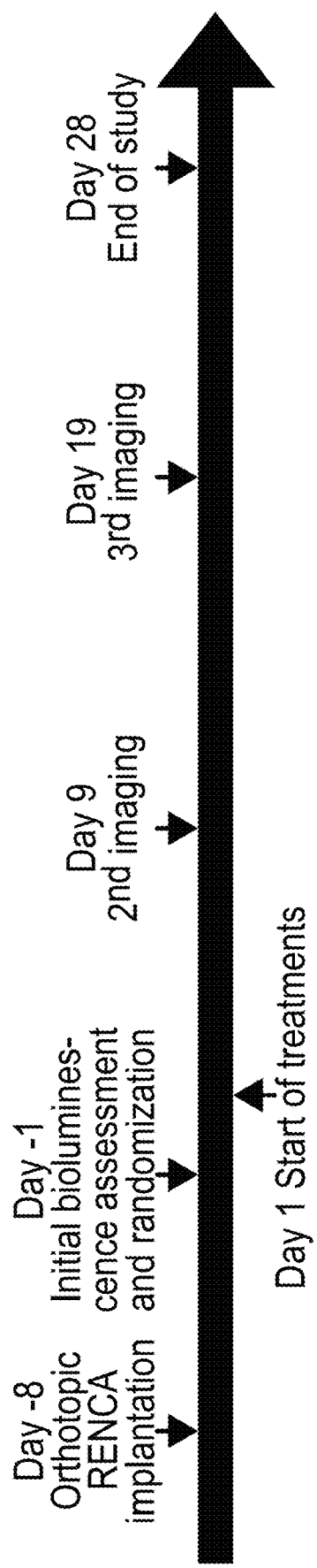
FIGS. 1A-1F show that entinostat improved immunotherapy in a syngeneic renal cell carcinoma mouse model.
Figure 1B:
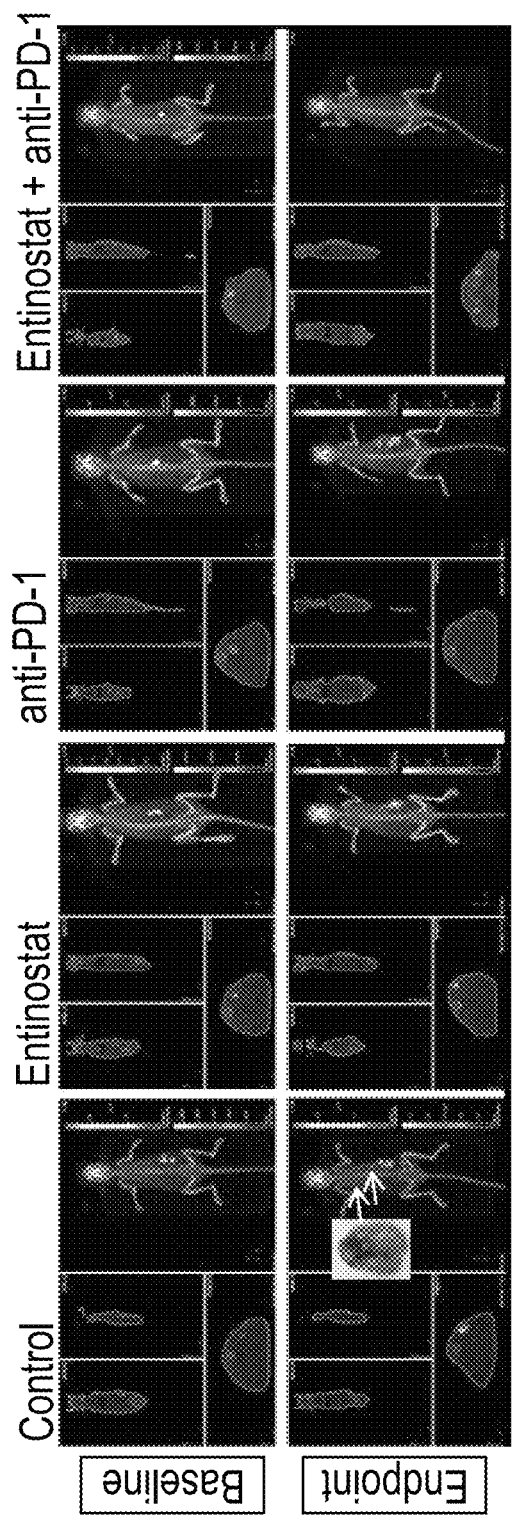
Figure 1C:
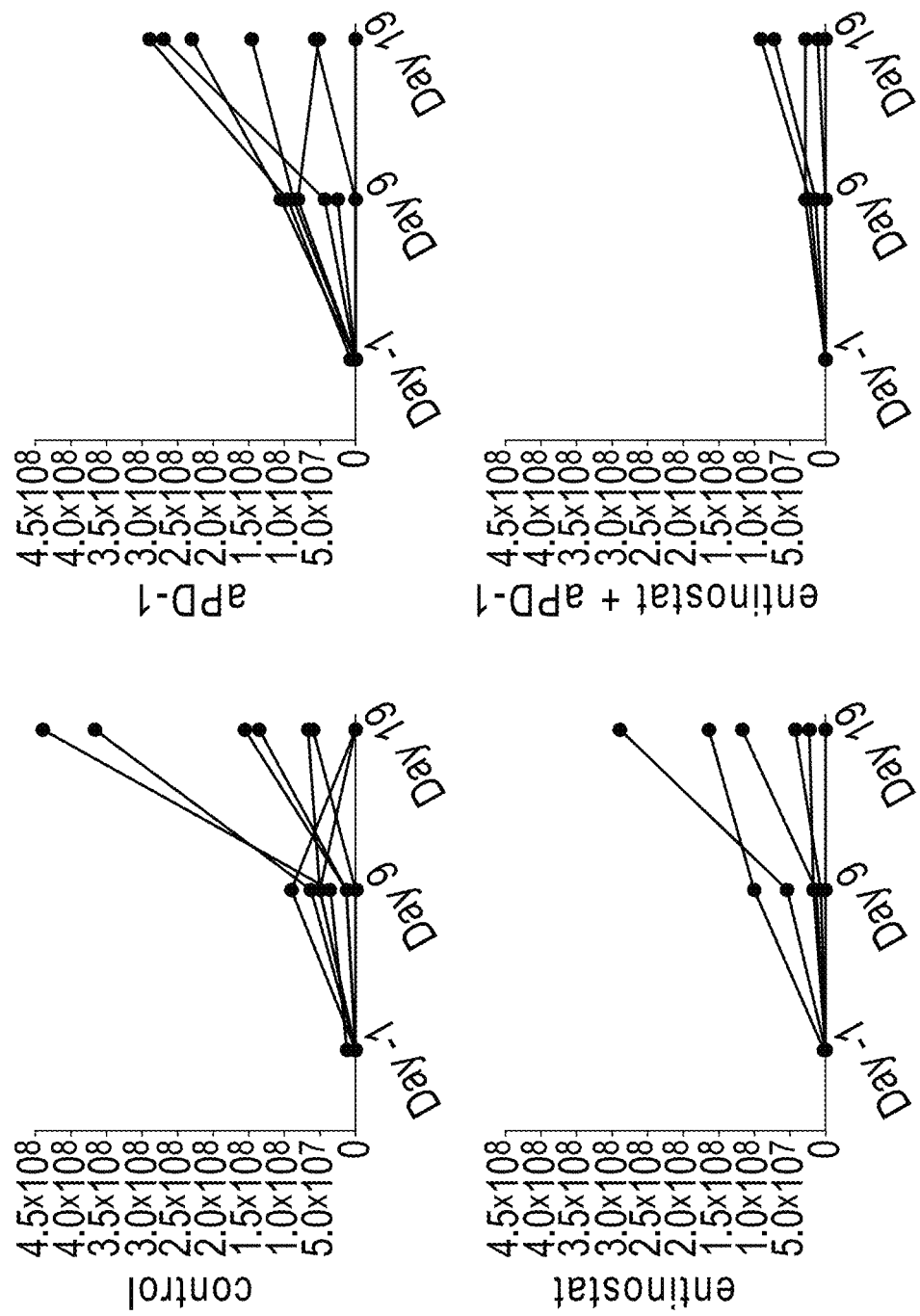
Figure 1D:
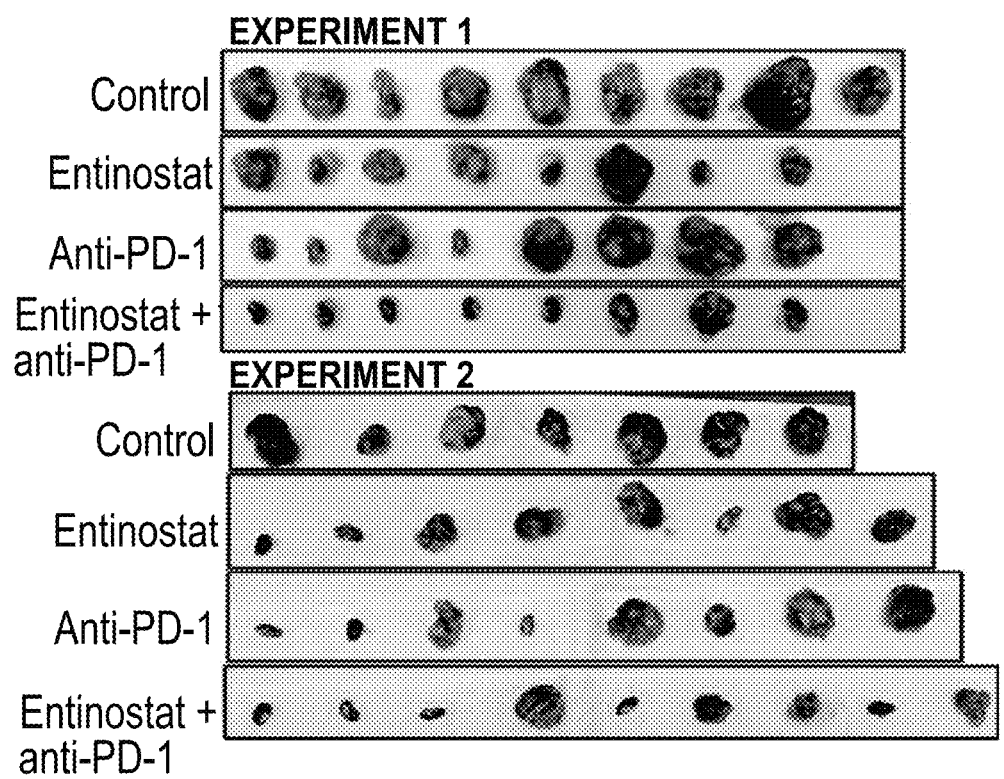
Figure 1E:
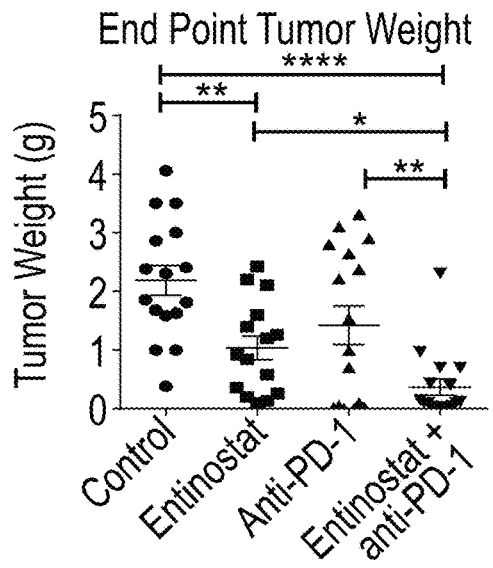

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Generally, the present disclosure is directed to a composition including the combination of a class I HDAC inhibitor and a PD-1 inhibitor. HDACs have been shown to be involved in oncogenic transformation by mediating the transcriptional regulation of genes that are involved in cell cycle progression, proliferation, and apoptosis. HDAC inhibitors are currently being developed for cancer treatment and have demonstrated antitumor activity in different tumors. HDACs have been characterized into four different classes with different targets and subcellular locations. It has recently been found that class I HDAC inhibitors induce STAT3 acetylation and consequently reduce FOXP3 transcription in Tregs. The inhibition of this key transcriptional factor leads to less function Tregs and unleashes the antitumor immune response.

One suitable selective class I HDAC inhibitor for use in the composition of the present disclosure includes the synthetic benzamide, entinostat (Pyridin-3-ylmethyl N-[[4-[(2-aminophenyl)carbamoyl]phenyl]methyl]carbamate). Entinostat, a synthetic benamide, has antitumor activity both in vitro and in vivo in several tumor models. Particularly, entinostat has been shown to disrupt the dynamic interactions between the tumor microenvironment and host immune surveillance. Tumor tissues classically avoid immune surveillance both by releasing a myriad of immune-suppressive factors and chemoattractants enabling tumor-promoting inflammation. HDAC treatment with a class I HDAC inhibitor has been shown to increase the immunogenicity of a tumor, countering one immune-suppressive mechanism Other suitable class I HDAC inhibitors include, for example, vorinostat (N-Hydroxy-N'-phenyloctanediamide) and Trichostatin A (TSA) ((2E,4E,6R)-7-[4-(Dimethylamino)phenyl]-N-hydroxy-4,6-dimethyl-7-oxo-2,4-heptadienamide), Dacinostat (also known as LAQ824) ((E)-3-(4-(((2-(1H-indol-3-yl)ethyl)(2-hydroxyethyl)amino) methyl)phenyl)-N-hydroxyacrylamide), butyrate, valproic acid (VPA), Belinostat (also known as PXD101) ((2E)-N-Hydroxy-3-[3-(phenylsulfamoyl)phenyl]prop-2-enamide), Panobinostat (also known as LBH589) ((2E)-N-hydroxy-3-[4-({[2-(2-methyl-1H-indol-3-yl)ethyl]amino}methyl)phenyl]acrylamide), pyroxamide, SK-7041 (4-(dimethylamino)-N-[[4-[(E)-3-(hydroxyamino)-3-oxoprop-1-enyl] phenyl]methyl]benzamide), SK-7068 (N-[[4-[3-(hydroxyamino)-3-oxoprop-1-enyl]phenyl]methyl]-4-pyrrolidin-1-ylbenzamide), Trapoxin A (Cyclo((S)-gamma-oxo-L-alpha-aminooxiraneoctanoyl-L-phenylalanyl-L-phenylalanyl-D-2-piperidinecarbonyl)), cyclic tetrapeptide hydroxamic acid analogues (CHAPs), depudecin (4,5:8,9-Dianhydro-1,2,6,7,11-pentadeoxy-D-threo-D-ido-undeca-1, 6-dienitol), Mocetinostat (also known as MGCD-0103) (N-(2-Aminophenyl)-4-[[(4-pyridin-3-ylpyrimidin-2-yl)amino] methyl]benzamide) and the like and combinations thereof.

Suitable dosages of the class I HDAC inhibitor will depend upon a number of factors including, for example, age and weight of an individual, at least one precise condition requiring treatment, severity of a condition, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result. Exemplary suitable dosages of class I HDAC inhibitors may include from about 0.5 µM to about 2 µM, including about 0.5 µM. In a further embodiment, an individual may be administered a class I HDAC inhibitor in combination with a PD-1 inhibitor in a dosage of class I HDAC inhibitor of about 5 mg/kg.

The compositions generally include a PD-1 inhibitor in combination with the class I HDAC inhibitor. PD-1 is a cell surface receptor that belongs to the immunoglobulin superfamily and is expressed on T cells and pro-B cells. PD-1 binds two ligands, PD-L1 and PD-L2. PD-1, functioning as an immune checkpoint, plays an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in Tregs. Suitable PD-1 inhibitors for use in the compositions of the present disclosure include nivolumab, pembrolizumab and the like, and PD-L1 inhibitors such as atezolizumab, and combinations thereof.

Suitable dosages of the PD-1 inhibitor will depend upon a number of factors including, for example, age and weight of an individual, at least one precise condition requiring treatment, severity of a condition, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result. One exemplary suitable dosage of PD-1 inhibitors may include about 1.0 µM. In a further embodiment, an individual may be administered a PD-1 inhibitor in combination with a class I HDAC inhibitor in a dosage of PD-1 inhibitor of about 10 mg/kg.

The combination of class I HDAC inhibitors and PD-1 inhibitors can be administered as a pharmaceutical composition further including one or more pharmaceutically acceptable carriers. As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the active compound from one organ or portion of the body, to another organ or portion of the body. Each carrier must be "acceptable" in the sense of being compatible with the other components of the composition (e.g., class I HDAC inhibitor, PD-1 inhibitor) and not injurious to the individual. Lyophilized compositions, which may be reconstituted and administered, are also within the scope of the present disclosure.

Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal, subretinal, subconjunctival), drop infusion preparations, or suppositories. These compositions can be prepared by conventional means, and, if desired, the active compound (i.e., class I HDAC inhibitors, PD-1 inhibitors) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of the synthetic compounds into prodrugs, and the like for alleviating, mediating, preventing, and treating the diseases, disorders, and conditions described herein.

In another aspect, the present disclosure relates generally to the administration of the compositions for suppressing Tregs and enhancing the antitumor effect. Accordingly, the compositions including the combinations of class I HDAC inhibitors and PD-1 inhibitors used in the methods of the present disclosure can be administered to a subset of individuals in need. As used herein, an "individual in need" refers to an individual at risk for or having cancer, and in particular, renal cell carcinoma, breast cancer, prostate cancer, melanoma, and the like. Additionally, an "individual in need" is also used herein to refer to an individual at risk for or diagnosed by a medical professional as having cancer. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein. In particular, the individual in need is a human. The individual in need can also be, for example, an animal such as, for example, a non-human primate, a mouse, a rat, a rabbit, a cow, a pig, and other types of research and/or companion animals known to those skilled in the art It should be understood by one skilled in the art that the composition can be administered as a single dosage or multiple dosages over a period of time. For example, the compositions can be administered daily, every other day, every third day, weekly or the like over a period of three days, five days, seven days, or more. Further, the compositions can be administered once a day or more than once a day, including twice a day, three times daily, or more times.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Example 1

In this Example, the immunomodulatory capabilities of entinostat treatment in combination with anti-PD-1 antibody treatment were analyzed.

Materials and Methods:

Cell lines: The RENCA-Luc murine renal cell carcinoma cell line, purchased from American Type Culture Collection (National Cancer Institute), was stably transfected with a luciferase reporter in the Pili laboratory. Cells were cultured using RPMI 1640 (Corning) with 10% fetal bovine serum (Corning) and 1% Pen/Strep (Life Technologies). Cells were incubated in an incubator maintained at 37° C. and 5% $CO_2$. 75-80% confluent cells were harvested for orthotopic injection into the kidney of Balb/c mice using 0.25% Trypsin (Corning) and suspended in a 1:1 ratio of MATRIGEL® (Corning) and DPBS (Gibco).

J774M cell line—contributed by Georgia Cancer Center/ culture methods.

The J774M cell line was cultured with DMEM (Corning) media with 10% fetal bovine serum (Corning) and 1% Pen/Strep (Life Technologies). Cells were incubated in 37° C. and 5% $CO_2$. 70-80% confluent cells were harvested using a cell scraper and passaged as suggested for the parent cell line via ATCC guidelines.

Tumor suspension and spleenocyte preparation: Live tumor sections were isolated from tumors, cut into small pieces, and digested with an enzyme cocktail solution from the mouse tumor dissociation kit (Miltenyi Biotec—130-096-730). Tumors were incubated with the enzyme cocktail for 30 minutes at 37° C. with agitation. The enzyme reaction was arrested using PBS, cells were spun at 300 g, 4° C. for 7 minutes, re-suspended in PBS and mashed through a 70 um cell strainer. Cells from these tumors were either used for flow cytometry analysis or further processed and used for functional analyses.

T cell isolation & activation: Whole spleens were harvested from naïve mice, mashed and passed through a 70 µm strainer. Cells were then washed, lysed with RBC lysis buffer (Affymetrix 00-4333-57), and cultured in RPMI medium with 10% FBS, Pen (100 units/ml)-Strep (100 mg/ml), 1 mM sodium pyruvate, 100 mM non-essential amino-acids, 2 mM L-Glutamine, 55 µM BME, with anti-CD3 (eBioscience 16-0031-85) and anti-CD28 (eBioscience 5012503) for approximately 24 hours. $CD8^+$ T cells were then isolated using a $CD8a^+$ T cell isolation kit from Miltenyi Biotec (130-104-075), stained with CFSE (NC9759757), according to the manufacturer's protocol, and co-cultured with MDSCs as described below.

MDSC Isolation: MDSCs were isolated from RENCA tumors of each group using Miltenyi Biotec's Myeloid Derived Suppressor Cell Isolation Kit (130-094-538) and co-cultured with isolated CD8$^+$ T cells in serially diluted concentrations.

T cell suppression assay: T cells ($1 \times 10^5$; isolated with a CD8a$^+$ T cell isolation kit; Miltenyi Biotec) were cultured in plates with varying numbers of either G-MDSCs or M-MDSCs isolated from RENCA tumors for 16-18 hours. T cells isolated in the listed method were co-cultured with entinostat treated J774M cells for 68-72 hours. Cells were then harvested, stained and analyzed via FACS analysis.

In vivo tumor growth (RENCA): All procedures were performed and approved in strict accordance with the Institutional Animal Care and Use Committee (IACUC) at Roswell Park Cancer Institute, Indiana University School of Medicine, and with the NIH Guide for the Care and Use of Laboratory Animal guidelines.

Female five- to six-week old Balb/c mice (Charles Rivers) were maintained in a temperature controlled room with a 12/12 hour light/dark schedule and food provided ad libitum. 70-80% confluent RENCA-Luc cells were harvested using 0.25% Trypsin (Corning) and suspended in a 1:1 ratio of matrigel (Corning) and HBSS (Gibco), 10 µl containing $1 \times 10^4$ cells was injected under the renal capsule. Following one week post-injection preliminary bioluminescent imaging, mice were randomized into four groups: control, entinostat, anti-PD-1, or combination. Mouse tumors were serially imaged using a bioluminescent IVIS imaging machine.

Entinostat and anti-PD-1 treatment: Mice in the treatment groups were treated orally with entinostat 5 mg/kg 5 days/week, I.P. with 10 mg/kg or 20 mg/kg ($2^{nd}$ survival study) from BioXCell, or a combination treatment regimen.

Cell staining and flow cytometry: Splenocytes, tumor cell suspensions, and peripheral blood cells were washed, blocked with Fc Block (anti-mouse CD16/32 mAb; BD Biosciences) at 4° C. for 15 minutes, and stained with fluorescence conjugated antibodies against surface markers: CD45 (clone 30-F11), CD11b (clone M1/70), Gr1 (clone RB6-8C5), Ly6C (clone AL-21), Ly6G (clone 1A8), F480 (clone BM8), CD8a (clone 53-6.7), CD4 (clone RM4-5) antibodies purchased from BioLegend, eBioscience or BD Biosciences. Cells were then fixed in Fixation/Permeabilization buffer (eBioscience) and stained with antibodies against intracellular proteins, including FoxP3 (NRRF-30) and Granzyme B (clone GB11). The antibodies were purchased from BD Biosciences, Biolegend, and R&D Systems and used in staining. Stained cells and isotype-control-stained cells, were assayed on a LSR4 or Fortessa flow cytometer (BD Biosciences). Data analysis was performed using the FlowJo (FlowJo LLC) and/or ModFit LT 4.1 software.

Proteome Profile: Tumor tissue was homogenized in PBS containing protease inhibitors. Following homogenization, Triton X-100 was added to a final concentration of 1%, frozen at −80° C., thawed, centrifuged as 10,000 g for 5 minutes, quantified and assayed according to the manufacturer's protocol. Blood samples were collected from mice in each cohort, allowed to clot for 2 hours at room temperature, centrifuged at 2000 g for 15 minutes. Serum samples were frozen at −80° C. until time of analysis at which time they were run according to manufacturer's protocol. All samples were processed and run on R&D Systems mouse XL cytokine array kit (Ary028).

Quantitative real-time PCR: mRNA was extracted from J774M cells that were treated±entinostat using standard Trizol protocols. RNA concentration and purity were determined through measurement of A260/280 ratios with a Synergy Hi Multi-Mode reader. cDNA was prepared using the iScript kit (Bio-Rad) and qPCR was performed using an Applied Biosystems 7900HT fast real time PCR system. Sequence Detection Systems software v2.3 was used to identify the cycle threshold (Ct) values and to generate gene expression curves. Data were normalized to Gapdh expression and fold change was calculated. The primers used for target genes were: Gapdh_foward 5'-AACTTTGGCATT-GTGGAAGG-3', Gapdh_reverse 5'-ACACATTGGGGG-TAGGAACA-3' (SEQ ID NO:1), Arginase 1_forward 5'-GTGAAGAACCCACGGTCTGT-3' (SEQ ID NO:2), and Arginase 1_reverse 5'-CTGGTTGTCAGGGGAGTGTT-3' (SEQ ID NO:3).

Results:

Entinostat enhanced the antitumor effect of PD-1 inhibition in a murine renal cell carcinoma model. Previous studies have indicated that entinostat treatment has the potential to enhance immunotherapy treatments via direct impact on the tumor microenvironment, including T regulatory cells. Further, it was previously shown that entinostat enhanced IL-2 immunotherapy by regulating T regulatory cell function by STAT3 acetylation in the RENCA model. To investigate the immunomodulatory potential of entinostat on the innate immune system, entinostate was used in combination with a mouse checkpoint inhibitor anti-PD-1 antibody in the RENCA model. The use of an anti-PD-1 immune checkpoint inhibitor impacts the tumor microenvironment (TME) as a whole with PD-L1 expression presented on both tumor and innate immune cells. The RENCA model has been shown to attract highly immunosuppressive MDSCs, a key factor in suppression of anti-tumor T cell activity. Balb/c mice were inoculated orthotopically with luciferin tagged RENCA cells.

Tumor bearing mice were randomized based on bioluminescent readouts and separated into four groups: control, entinostat (5 mg/kg), anti-PD-1 (10 mg/kg), or the combination of entinostat and anti-PD-1. Treatment with entinostat alone resulted in significant inhibition of tumor growth (52.6% growth inhibition; entinostat vs. control: p=0.0015), while anti-PD-1 alone only moderately reduced tumor growth (35.05% growth inhibition; anti-PD-1 vs. control: p=0.0768) (FIGS. 1A-1E). Additionally, the combination of entinostat and anti-PD-1 treatment enhanced tumor growth inhibition compared to the control and each of the single treatment groups (83.3% reduction; combination vs. vehicle: p<0.0001; combination vs. entinostat: p=0.0115; combination vs. anti-PD-1: p=0.0076) (FIGS. 1A-1E).

Figure 1F:
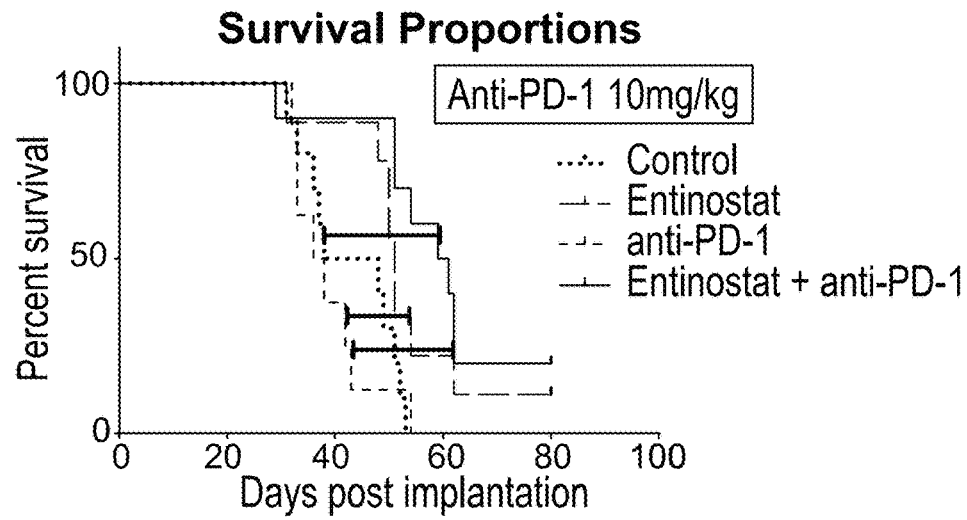
Figure 1F:
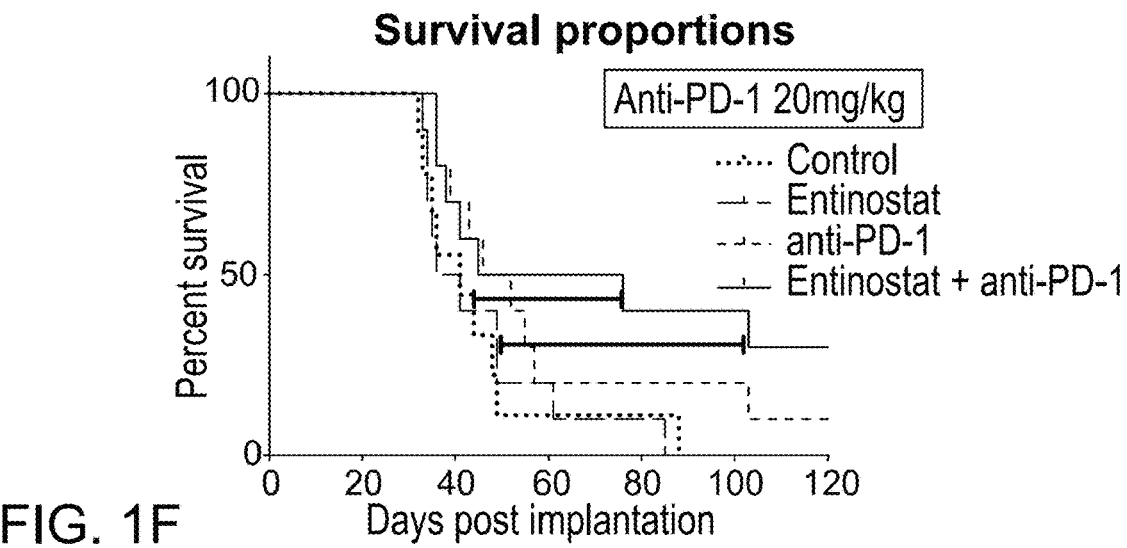

Clinically, anti-PD-1 immunotherapy has shown prolonged stabilization of disease in up to 41% of patients with RCC. Following the previous study, the survival enhancing effects of the entinostat and anti-PD-1 antibody combination were analyzed. Using the treatment concentrations previously described, a significant increase in the survival of mice was observed. Combination treatment resulted in significant increase of survival (combination vs. anti-PD-1: p=0.0012; combination vs. control: p=0.0009) (FIG. 1F). It was next examined whether increasing the dose of anti-PD-1 antibody treatment would further enhance the response of the RENCA tumor model. The results showed prolonged survival in the anti-PD-1 group and an enhanced effect in the combination treated cohort as compared to the control and entinostat groups (combination vs. control: p=0.0471; combination vs. entinostat: p=0.0372) (FIG. 1F). The results of these studies suggest that combination of entinostat with anti-PD-1 antibody immunotherapy may promote survival in the murine ccRCC model RENCA.

Figure 2A:
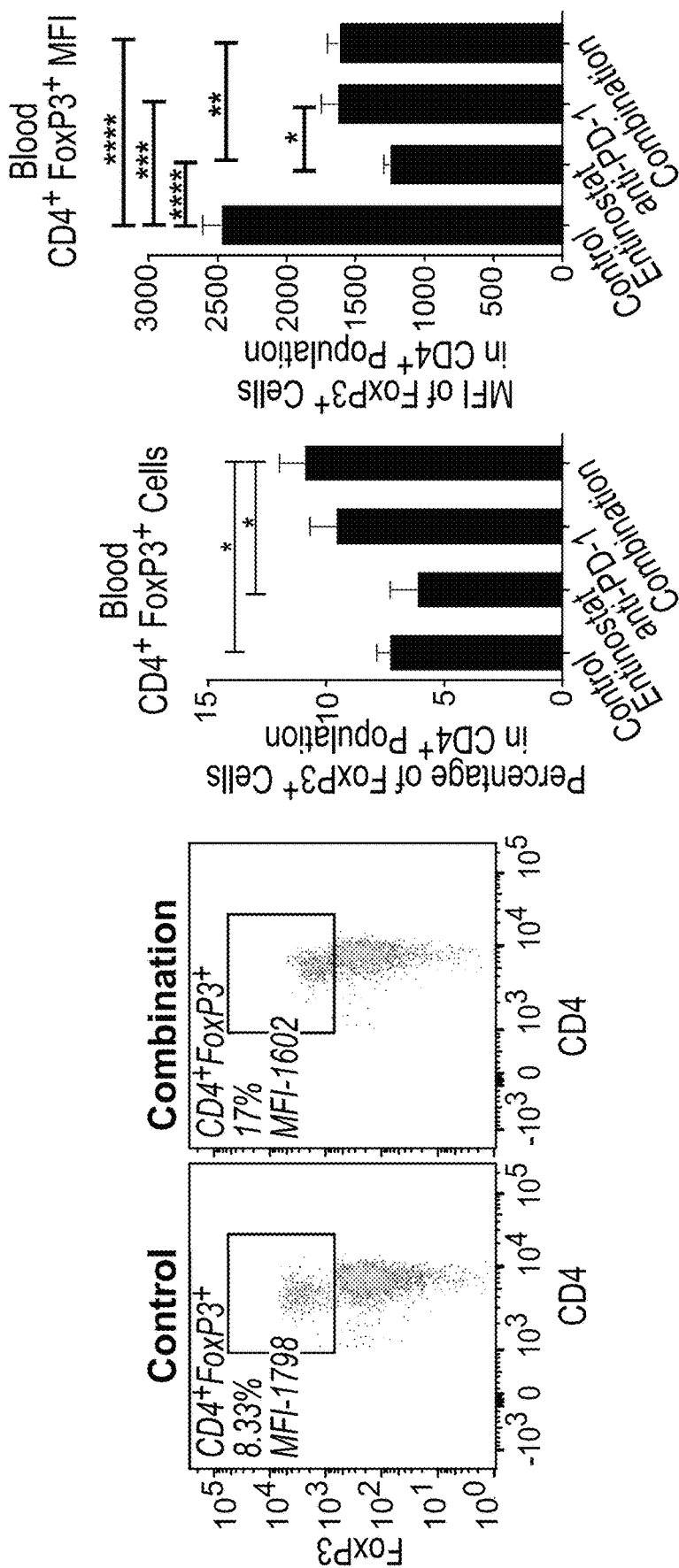
FIGS. 2A & 2B show that entinostat modulated T cell and tumor associated macrophage response in the syngeneic ccRCC mouse model, RENCA. Blood and tumor samples were isolated from mice at the end of Example 2 and processed for flow cytometry analysis.
Figure 2B:
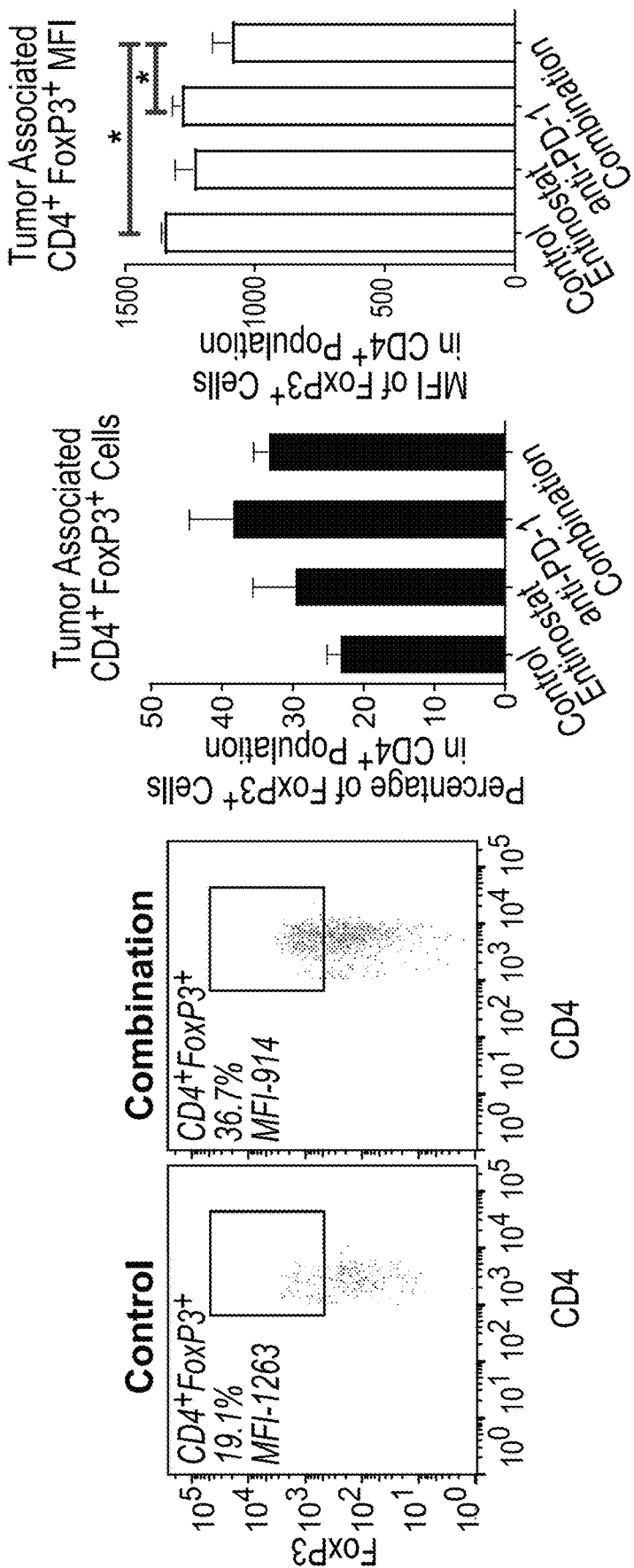

Enhanced anti-PD-1 immunotherapy is associated with increased antitumor immune responses and decreased presence of immunosuppressive cell populations. The PD/L-1 axis plays a central role in assisting tumor evasion of immune surveillance via promotion of activated T cell apoptosis. Additionally, HDAC inhibition (HDACi) treatment has been shown to alter the tumor microenvironment by reducing Treg cell activity and enhancing CD8 T cell infiltration. To understand whether the inhibition of tumor growth resulting from the combination, treatment was associated with an enhanced immune response, the circulating and tumor infiltrating immune populations were examined. End-point blood and tumor samples were collected from mice in each arm of this Example and subjected to immunofluorescence staining and FACS analysis. Increased Treg, $CD4^+FoxP3^+$, presence in the blood and no significant difference in the TME was observed. However, as previously shown, HDAC inhibition treatment resulted in a significant decrease in the protein levels of FoxP3 in the circulating $CD4^+FoxP3^+$ cell subtype, as represented by the MFI (mean fluorescence intensity). The combination group, while also showing a reduction in FoxP3 protein levels was not significantly reduced as compared to the control or anti-PD-1 group alone in the blood samples (FIG. 2A). In the TME, a significant reduction in the MFI of $CD4^+FoxP3^+$ cells was observed, suggesting an inhibition of the Treg function in response to anti-PD-1 and entinostat combination treatment (FIG. 2B).

Figure 2C:
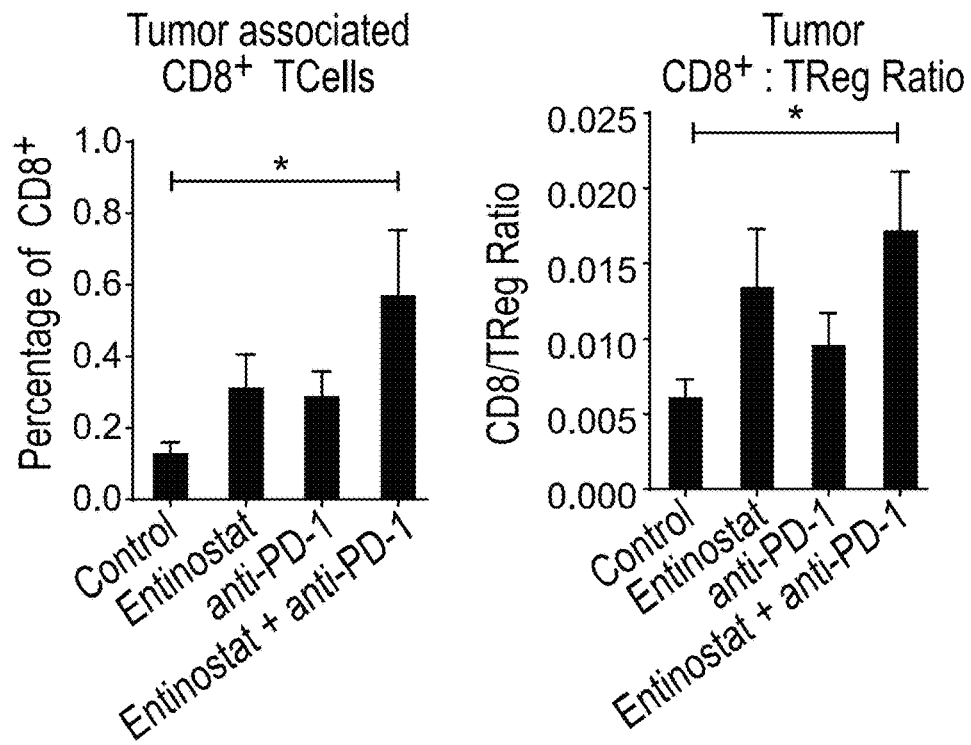
FIG. 2C depicts the quantitative FACS analysis of CD8$^+$ T cell infiltrates into the TME. The results show a significant increase in CD8$^+$ infiltration and in the CD8$^+$:T regulatory cells ratio.

CD8 T cells are critical components of the PD/L-1 axis and are crucial to tumor surveillance. When the PD/L-1 checkpoint axis is blocked there is often an increase in T cell function and tumor infiltration. The combinatorial effect of entinostat and anti-PD-1 immunotherapy was found to result in a significant increase in tumor infiltrating $CD8^+$ T cells (control vs. combination: p=0.0352) (FIG. 2C, left) Similarly, a statistically significant increase in the $CD8^+$ T cell:T regulatory cell ratio was observed, suggesting the generation of a less tumor suppressive environment (control vs. combination: p=0.0218) (FIG. 2C, right).

Figure 2D:
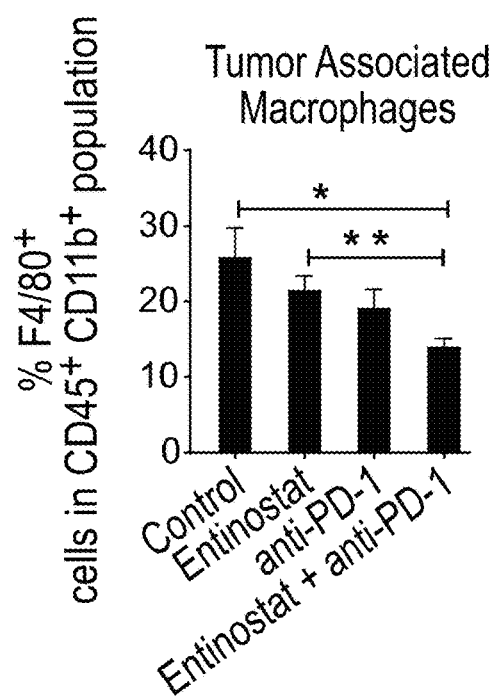
FIG. 2D depicts the quantitative FACS analysis results of tumor associate macrophage infiltration into the TME, showing a significant decrease in macrophage infiltration and indicating HDACi may impact the innate immune system. n=3-5 tumors/blood samples per cohort per panel. Results are shown as mean±SEM (*p<0.05; p<0.01; *p<0.001; ****p<0.0001), statistics were calculated using unpaired t test with Welch's correction.

Tumor associated macrophages (TAMs) support an immunosuppressive TME. Upon migration of immature myeloid cells to the tumor, these cells are often primed to become TAMs in response to chemokine and cytokine release from the tumor cells. These cells are marked by the pan-macrophage marker F4/80 in combination with $CD45^+$ $CD11b^+$ markers. Therefore, the presence of TAMs in response to entinostat and anti-PD-1 immunotherapy was examined, and a significant reduction in TAM presence was observed in the combination group as compared to the control and the entinostat alone (combination vs. control: p=0.0272; combination vs. entinostat: p=0.009) (FIG. 2D). Taken together, these results suggest that HDAC inhibition combination with anti-PD-1 immunotherapy significantly alters the suppressive nature of the tumor microenvironment and allows for increased immune response in the RENCA model.

Myeloid derived suppressor cell function is impaired by combination of entinostat and anti-PD-1 immunotherapy. Myeloid derived suppressor cells (MDSCs) are derived from immature myeloid cells which contribute to the immune suppressive TME by inhibiting anti-tumor T cell immune responses. MDSCs are present in two well defined, immunosuppressive sub-populations, granulocytic $Ly6G^+Ly6C^+$ (G-MDSCs) and monocytic $Ly6C^+Ly6G^-$ (M-MDSCs) MDSCs. The tumor attracts MDSCs, monocytes, and immature myeloid cells via release of chemoattractants, such as CCL2, CCL5, CCL7, & CXCL12. MDSCs have been shown to protect and enhance the immune escape of the tumor via multiple mechanisms including, upregulation of surface PD-L1, production of immunosuppressive cytokines (IL-10, TGF-β) & T reg attracting cytokines (CCL4, CCL5), elevation of arginase 1 (Arg1) & iNOS, and resistance to cytotoxic T cells.

Figure 3A:
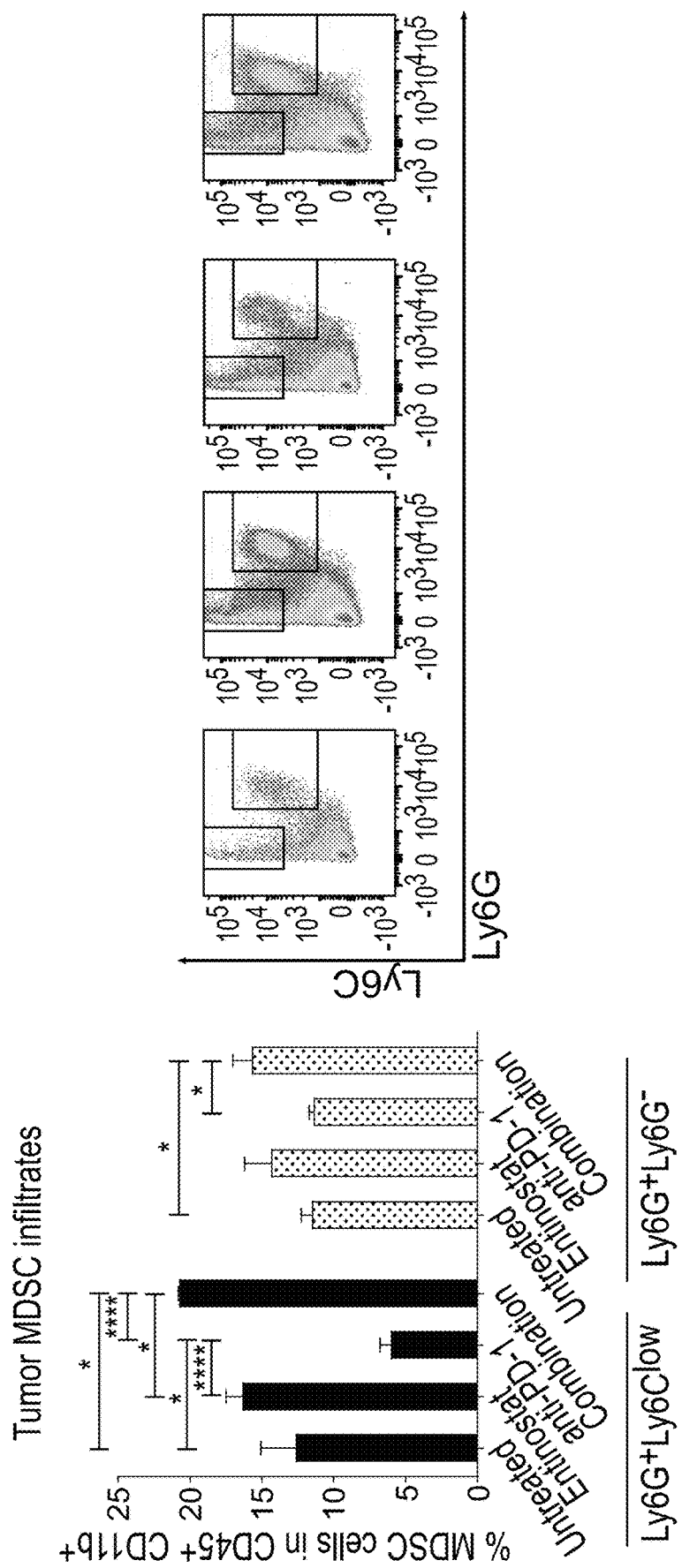
FIGS. 3A-3F shows that entinostat inhibited the immunosuppressive capacity of MDSCs collected from RENCA tumors.
Figure 3B:
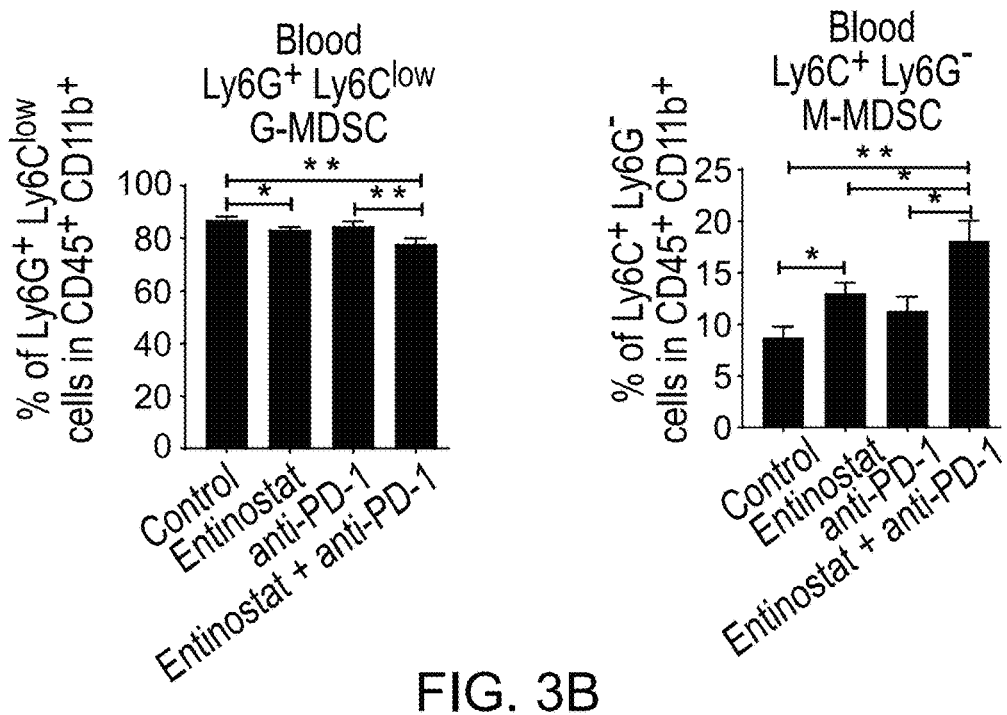

A slight increase was observed in tumor infiltrating G-MDSC and M-MDSC populations with entinostat single treatment (entinostat vs. control: G-MDSC p=0.2025, M-MDSC p=0.1903), while anti-PD-1 single agent treatment led to a reduction in the G-MDSC populations (anti-PD-1 vs. control: G-MDSC p=0.0.0402,) (FIG. 3A). The slight increase in MDSC populations first observed in the entinostat group was amplified in the combination group where a trend of increased presence across in both populations (combination vs. control: G-MDSC p=0.0199, M-MDSC p=0.0222; combination vs. entinostat: G-MDSC p=0.0102, M-MDSC p=0.5613; combination vs. anti-PD-1: G-MDSC p=0.0001, M-MDSC p=0.0198) was observed (FIG. 3A). Additionally, alterations in the circulating MDSCs with slight decreases in the circulating G-MDSCs and significant increases in the circulating M-MDSCs following entinostat or combination treatments (entinostat vs. control: G-MDSC p=0.0421, M-MDSC p=0.0188; entinostat vs. combination: G-MDSC p=0.0608, M-MDSC p=0.0500; anti-PD-1 vs. combination: G-MDSC p=0.0424, M-MDSC p=0.0229; combination vs. control: G-MDSC p=0.0080, M-MDSC p=0.0049) was observed (FIG. 3B). Thus, it has been shown that entinostat may enhance the effect of anti-PD-1 immunotherapy treatment in the RENCA model with alterations of both the peripheral immune status and that of the tumor microenvironment. To further examine the mechanism of this effect the intriguing alterations seen in the MDSC compartment of the immune system were further analyzed.

Figure 3C:
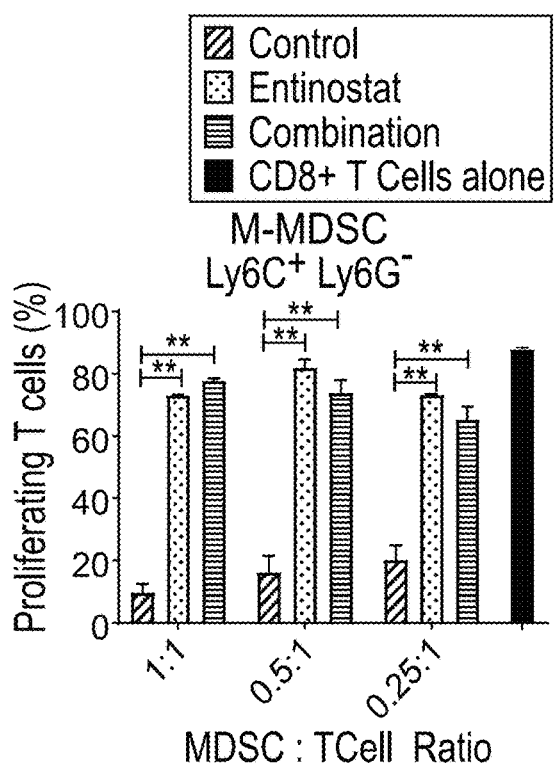
Figure 3D:
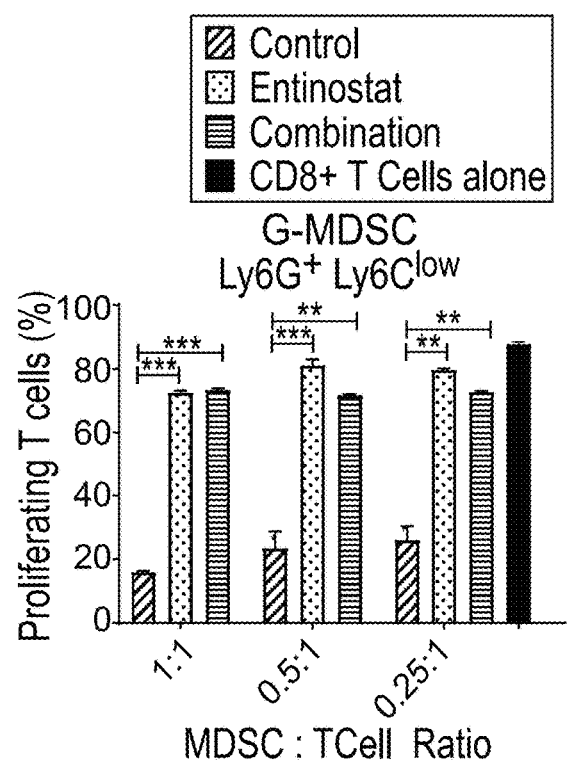
Figure 3E:
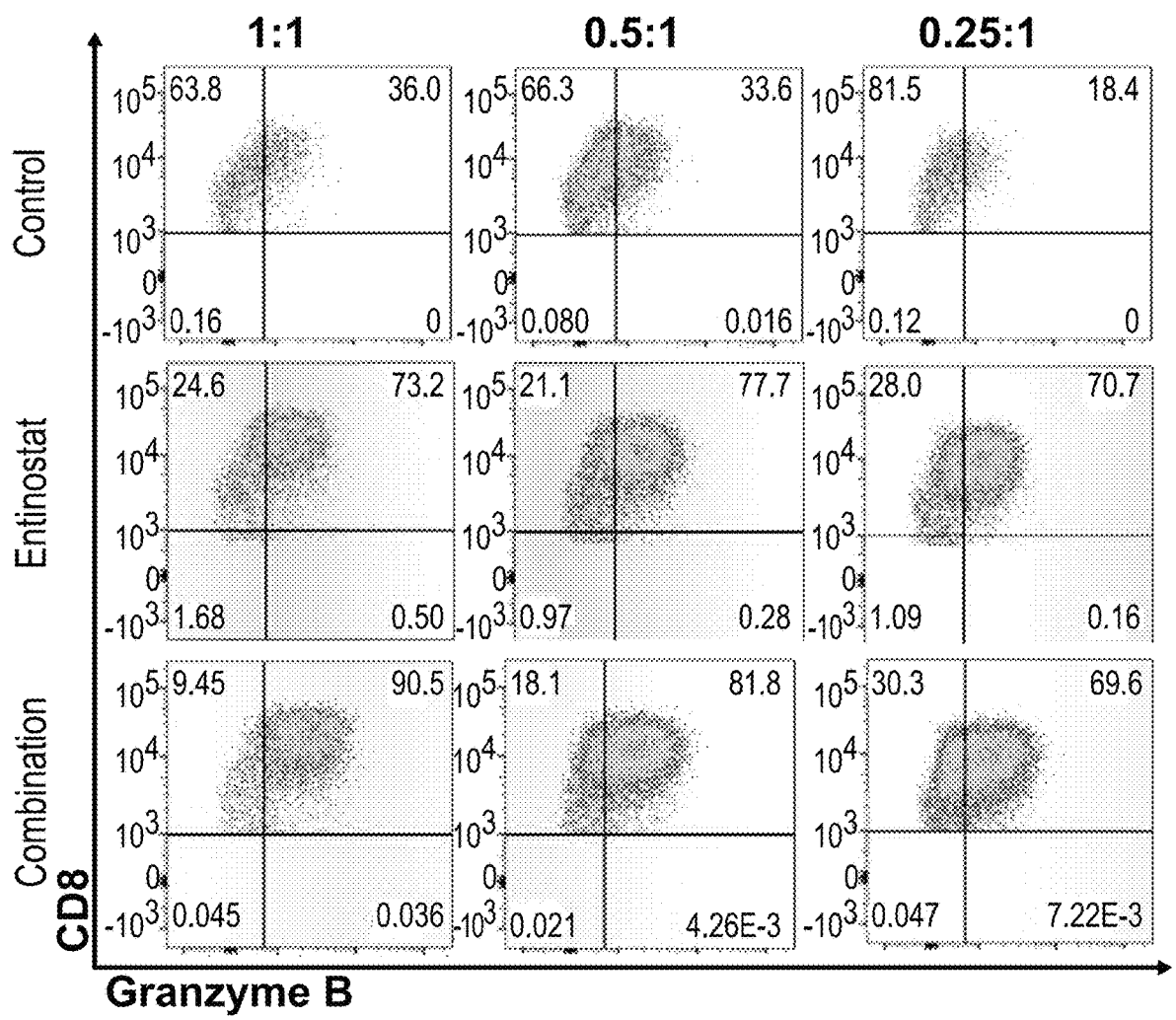
Figure 3F:
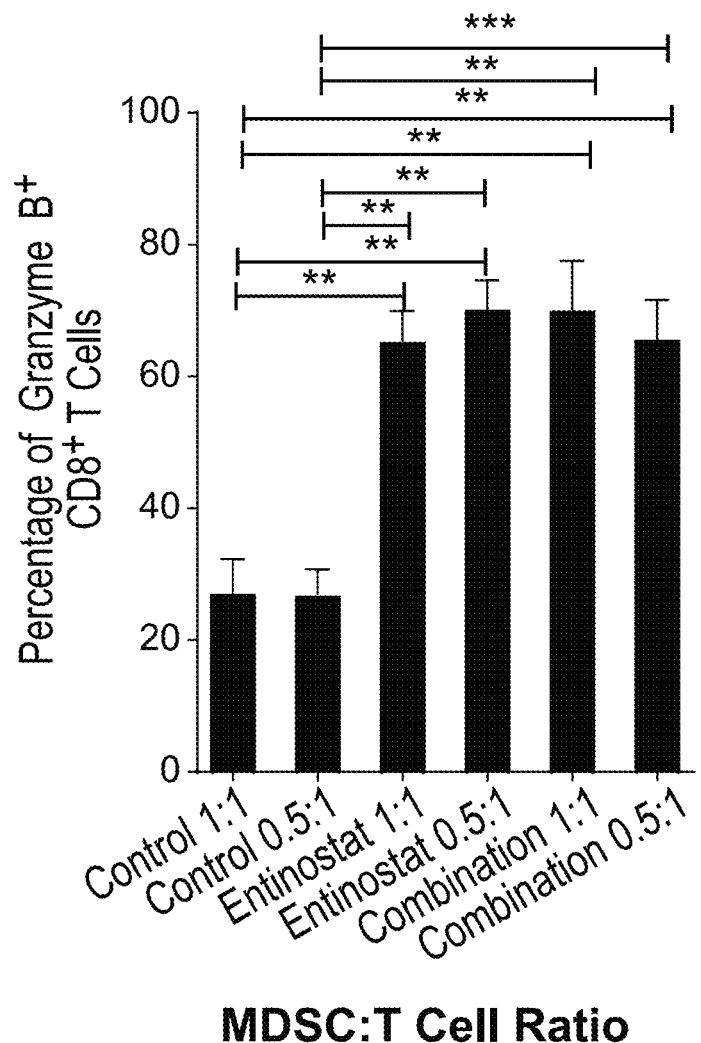

To determine whether treatment specific increases in MDSC infiltrates were associated with altered function of MDSC suppressive capabilities, the ability of tumor associated MDSCs to suppress pre-activated $CD8^+$ T cells from a tumor naïve mouse was tested ex vivo. Consistent with the in vivo data showing enhanced survival and tumor inhibition of mice implanted with RENCA tumors, it was observed that, following entinostat or combination treatment, the MDSCs (G-MDSC or M-MDSC) displayed a significant reduction in their capacity to inhibit $CD8^+$ T cell proliferation. In each of the MDSC to T cell ratios, 1:1, 0.5:1, & 0.25:1, there was a statistically significant (p-value≤0.01 for each of the G-MDSC and M-MDSC conditions) reduction in MDSC inhibition of $CD8^+$ T cell proliferation when pre-stimulated (anti-CD3/CD28 stimulated) cells were co-cultured with MDSCs isolated from the TME for 16-18 hours (FIGS. 3C & 3D). The shorter co-culture time point was chosen here to avoid potentially altering the immunosuppressive status of these cells from the in vivo TME. These cells, isolated from the tumor of a treated mouse, were unable to inhibit the proliferation of the $CD8^+$ T cells such that they proliferated similarly to control stimulated $CD8^+$ T cells alone (~90% proliferation). Further examination of the $CD8^+$ T cells from these co-culture experiments revealed increased Granzyme B production by approximately 40% compared to the control group, in which MDSCs from an untreated tumor-bearing mouse were co-cultured with pre-stimulated $CD8^+$ T cells (p-value <0.01 for each condition and MDSC:T cell ratio). (FIGS. 3E & 3F). Together, these data indicate a substantial alteration in the function of tumor infiltrating MDSCs in response to entinostat treatment alone and in combination with anti-PD-1 immunotherapy. It has been shown that entinostat is capable of altering the tumor microenvironment by inhibiting FoxP3 function and these data show an additional modification of the TME via functional inhibition of MDSCs in a syngeneic mouse model of ccRCC.

Figure 4A:
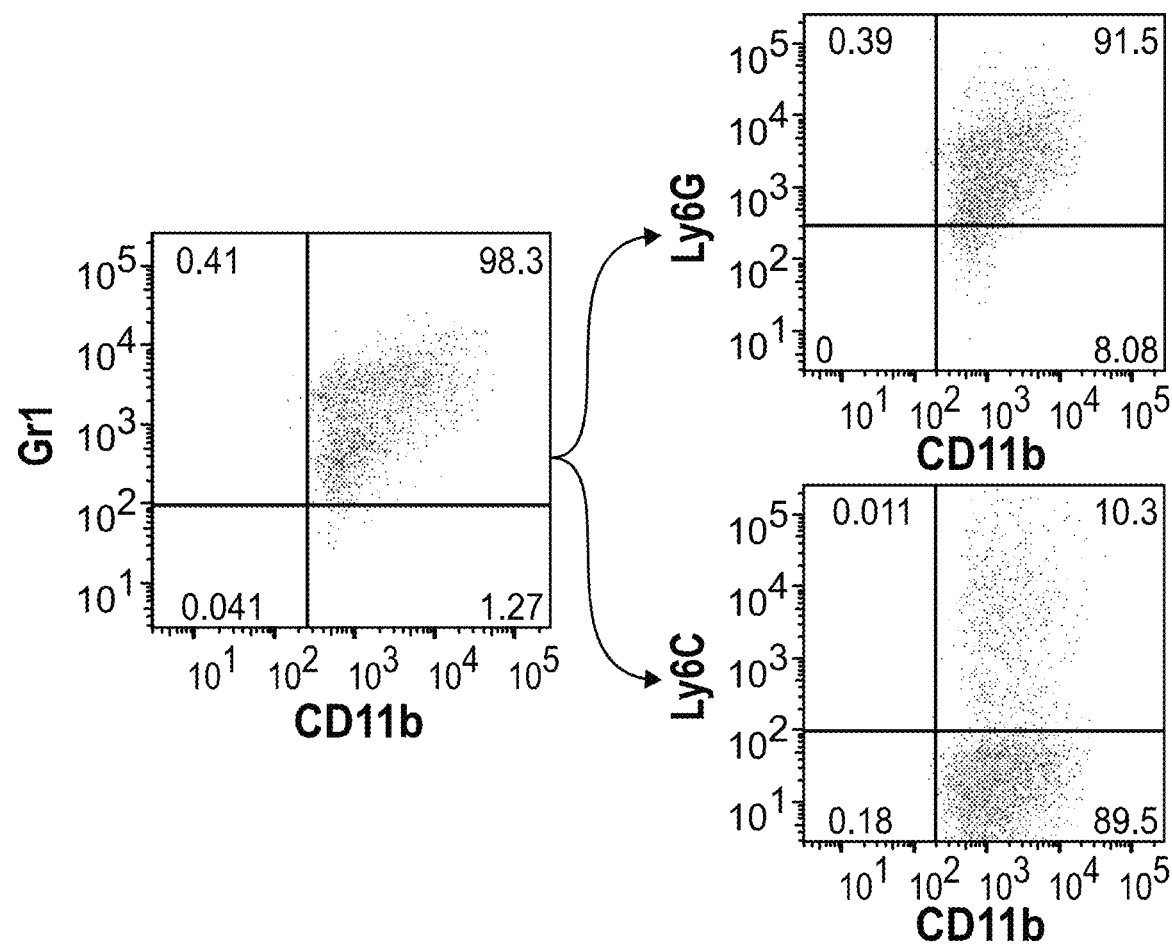
FIGS. 4A-4E show that entinostat diminisheed inhibitory capabilities of the MDSC-like cell line J774M.
Figure 4B:
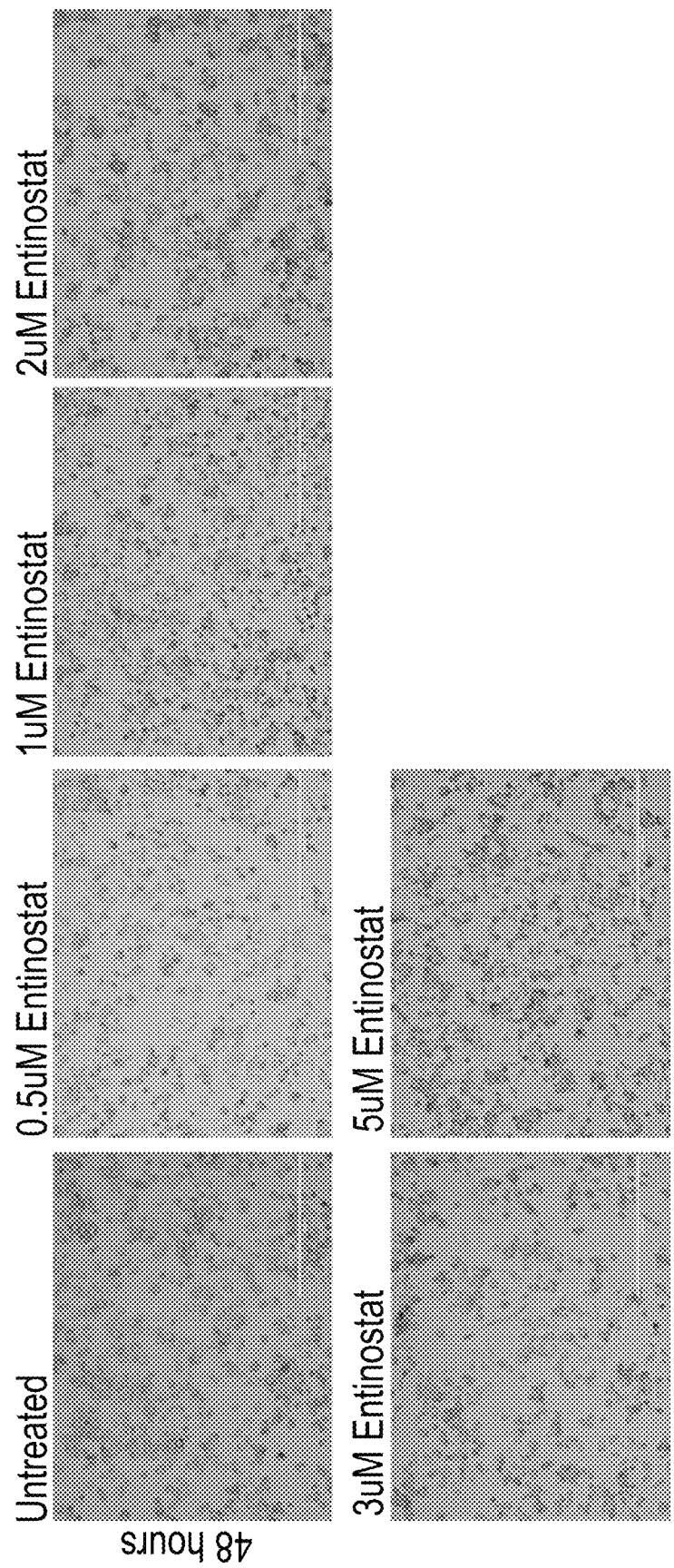
Figure 4C:
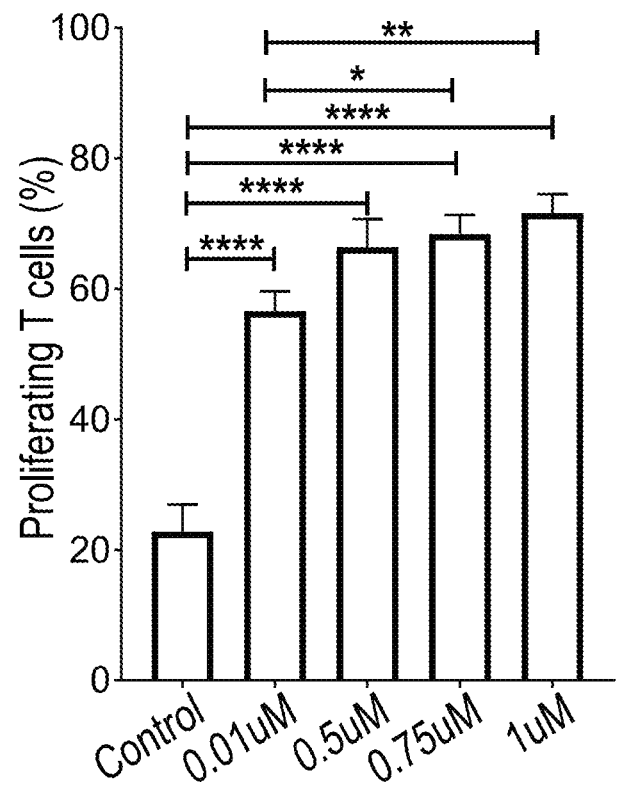
Figure 4D:
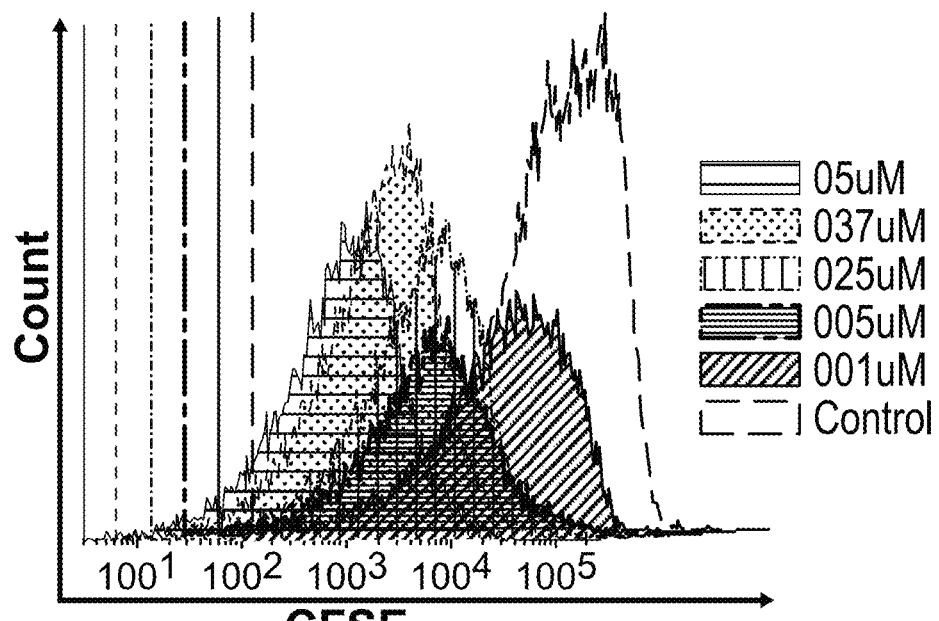
Figure 4E:
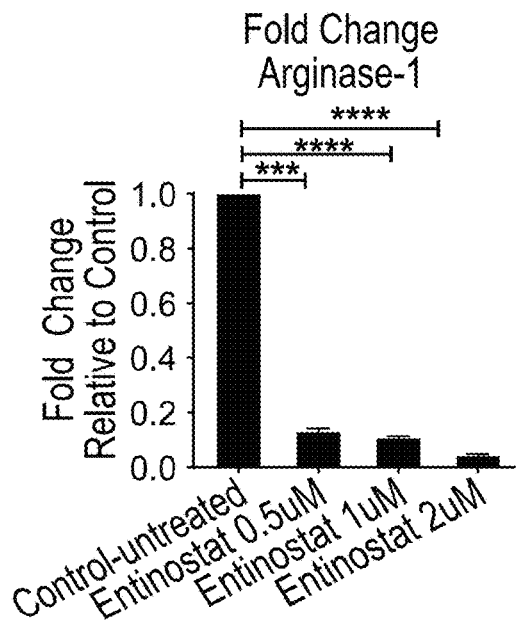
Figure 4G:
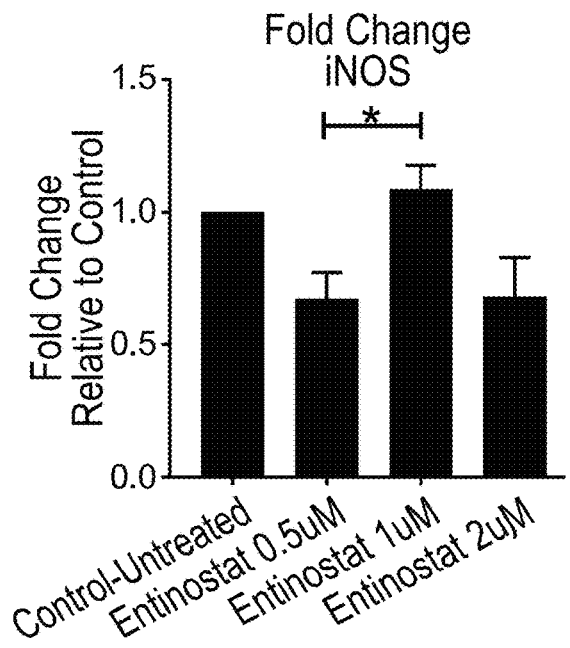
(FIG. 4G) Quantitative analysis depicting fold change of iNOS when J774M cells are treated with entinostat. Results are shown as mean±SEM (*p<0.05; p<0.01; *p<0.001; ****p<0.0001), statistics were calculated using unpaired t test with Welch's correction.
Figure 4F:
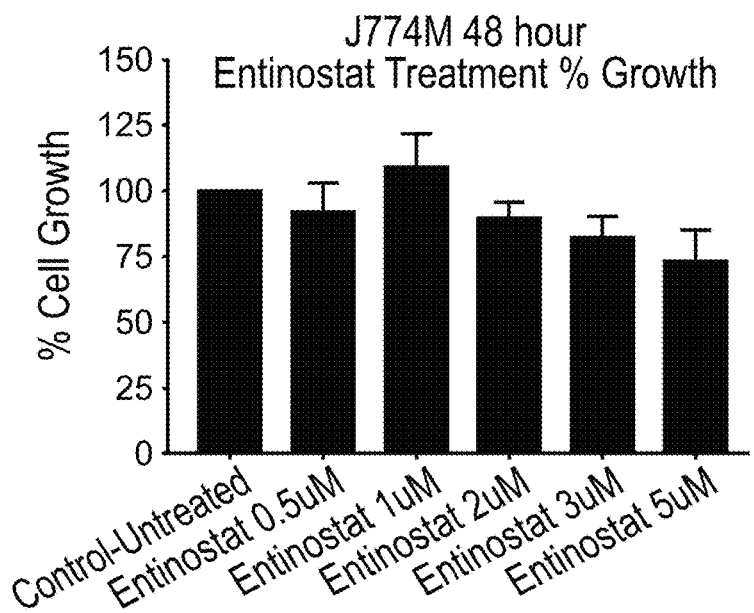
(FIG. 4F) Analysis of J774M cell proliferation or viability after 48 hours of entionstat treatment.

Entinostat treatment of MDSC-like cell line, J774M revealed arginase 1 as a potential mechanistic target. The J774M cell line, kindly supplied by the Kebin Liu laboratory at Georgia Cancer Center, Augusta University, has recently been characterized as a stable MDSC-like cell line. To validate these findings for the purposes of the instant Example, these cells were stained for Ly6C and Ly6G to further elucidate the MDSC-like status of the cells. It is shown in FIG. 4A, that the subpopulation ratio of these cells closely resembles what is found in the RENCA TME. Of the $CD45^+CD11b^+Gr1^+$ populations, ~90% of the cells are G-MDSC ($Ly6G^+$) and ~10% of the cells are M-MDSC ($Ly6C^+$) positive cells. Following this validation of the cell phenotype, the capability of these MDSC-like cells to be functionally altered with treatment of entinostat in vitro was studied. The cells were treated for up to 48 hours with concentrations ranging from 0.01-5 µM of entinostat with no significant alteration in J774M cell proliferation or viability (FIG. 4F). Co-culture of entinostat treated J774M cells with pre-activated $CD8^+$ T cells for 68-72 hours revealed significant increase in $CD8^+$ T cell proliferation nearing that of $CD8^+$ T cells alone, this Example is representative of three independent replicates (FIGS. 4B-4C). Further investigation of the J774M cells from these in vitro experiments revealed a significant inhibition of arginase-1 (Arg1) expression in the entinostat treated MDSC-like cells as compared to the control—untreated cells (control vs 0.5 µM entinostat: p=0.003; control vs 1 µM entinostat: p=0.0041; control vs 2 µM entinostat: p=0.0043) (FIG. 4D). MDSCs characteristically have heightened levels of arginase 1 and iNOS. While the assessment of iNOS yielded inconclusive results (FIG. 4G), the heightened activity of Arg1 allows for induction of cell cycle arrest in the cytotoxic T cell population via arg1 conversion of circulating L-arginine pools to urea and L-ornithine, thus reducing the presence of extra-cellular L-arginine, which is necessary for cytotoxic T cell survival. These data indicate that entinostat directly impairs the tumor-promoting, T cell inhibiting activity of MDSCs, with arginase 1 as a potential specific target.

Entinostat treatment primes the tumor microenvironment (TME) for enhanced response to immunotherapy. The tumor microenvironment takes advantage of the host immune system by recruiting and altering the function of immune cells. Chemokines and cytokines released by the tumor or tumor infiltrating cells prompt immune cell trafficking into the tumor microenvironment. Among those which lead to enhanced MDSC infiltration are CCL2 (JE/MCP-1), CCL5, CCL12 (MCP-5), CXCL12 (SDF-1) & VCAM-1. Once these cells are recruited into the TME, they expand and become activated in response to tumor derived factors, including M-CSF, G-CSF, GM-CSF, C5a, IL1-β, IL-10, & IL-6. MDSCs can then assist the tumor in growth, proliferation, angiogenesis, and escape of immune surveillance via upregulation of arginase-1 and iNOS, as well as production of related cytokines (i.e., Treg promoting IL-10, CCL4, CCL5). The TME is an intricate system with a continual storm of cytokines being released and interpreted by both the tumor cells and the associated immune infiltrates. Understanding this complex balance and how it is altered with HDAC inhibition and immunotherapy is of key interest.

Figure 5A:
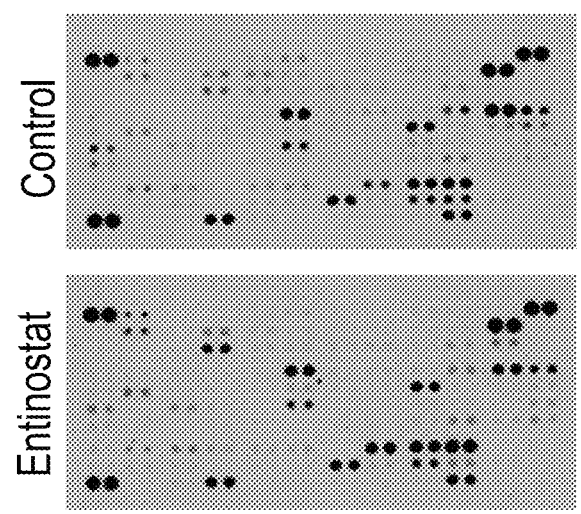
FIGS. 5A-5E depict that treatment with entinostat significantly altered the highly immunosuppressive environment found in RENCA tumors. Tumor and blood samples collected from mice at the end of Example 2 were processed and examined using the Proteome Profiler Mouse XL Cytokine array kit (Ary028).
Figure 5B:
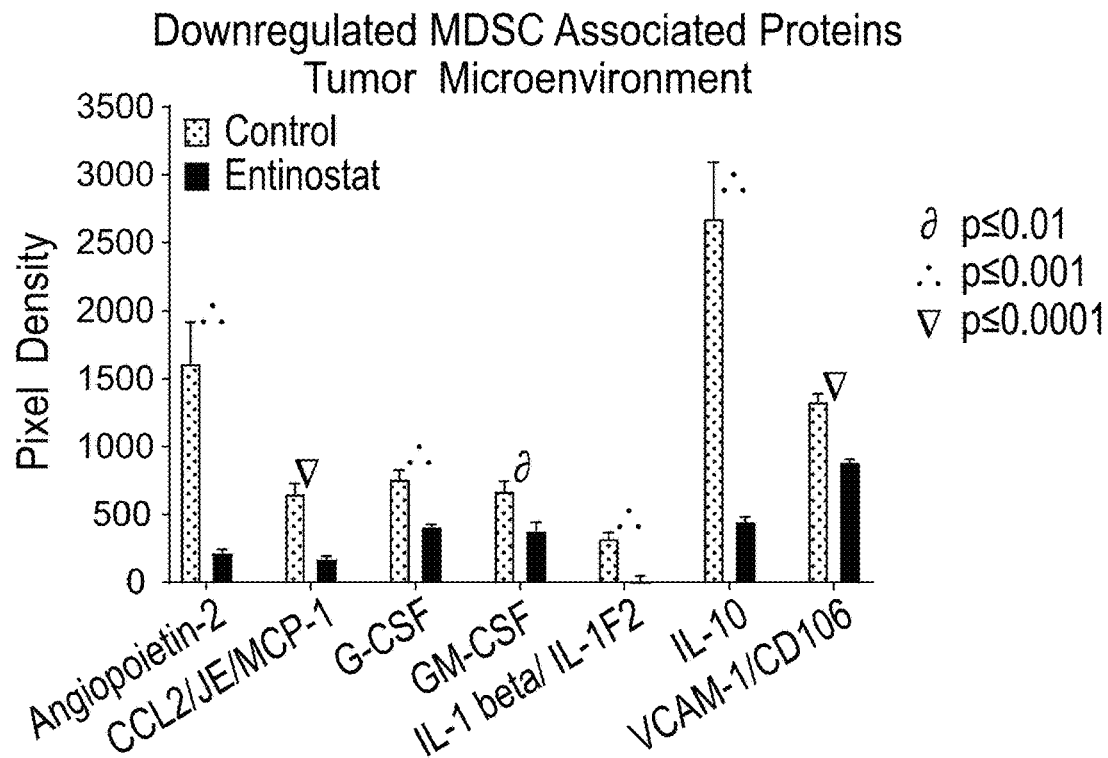
Figure 5C:
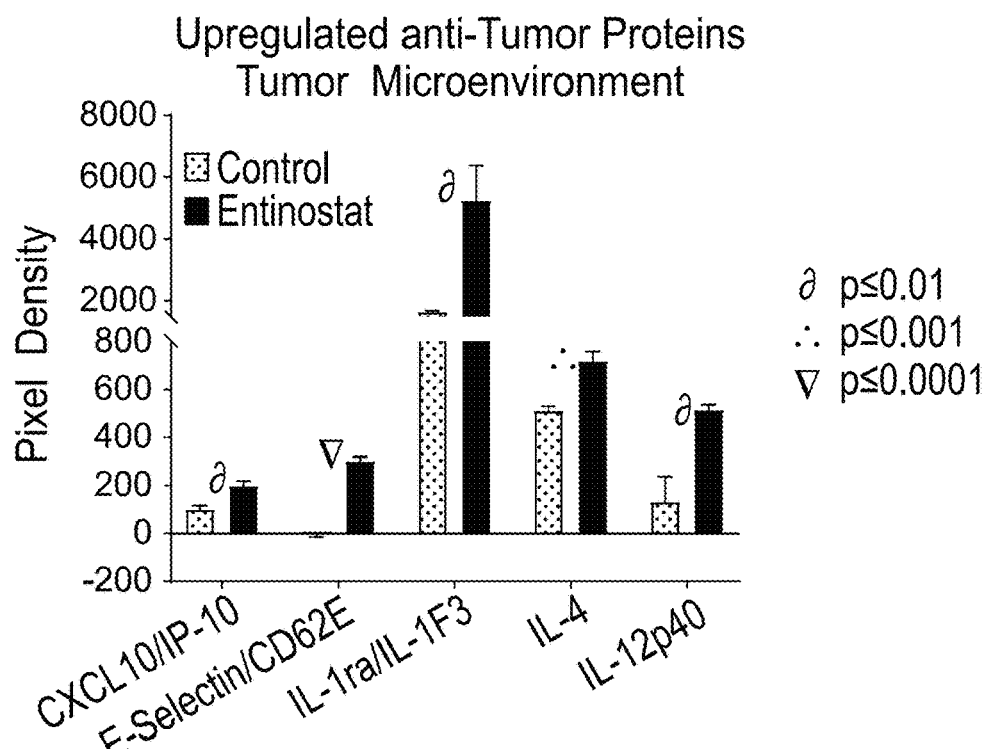
Figure 5D:
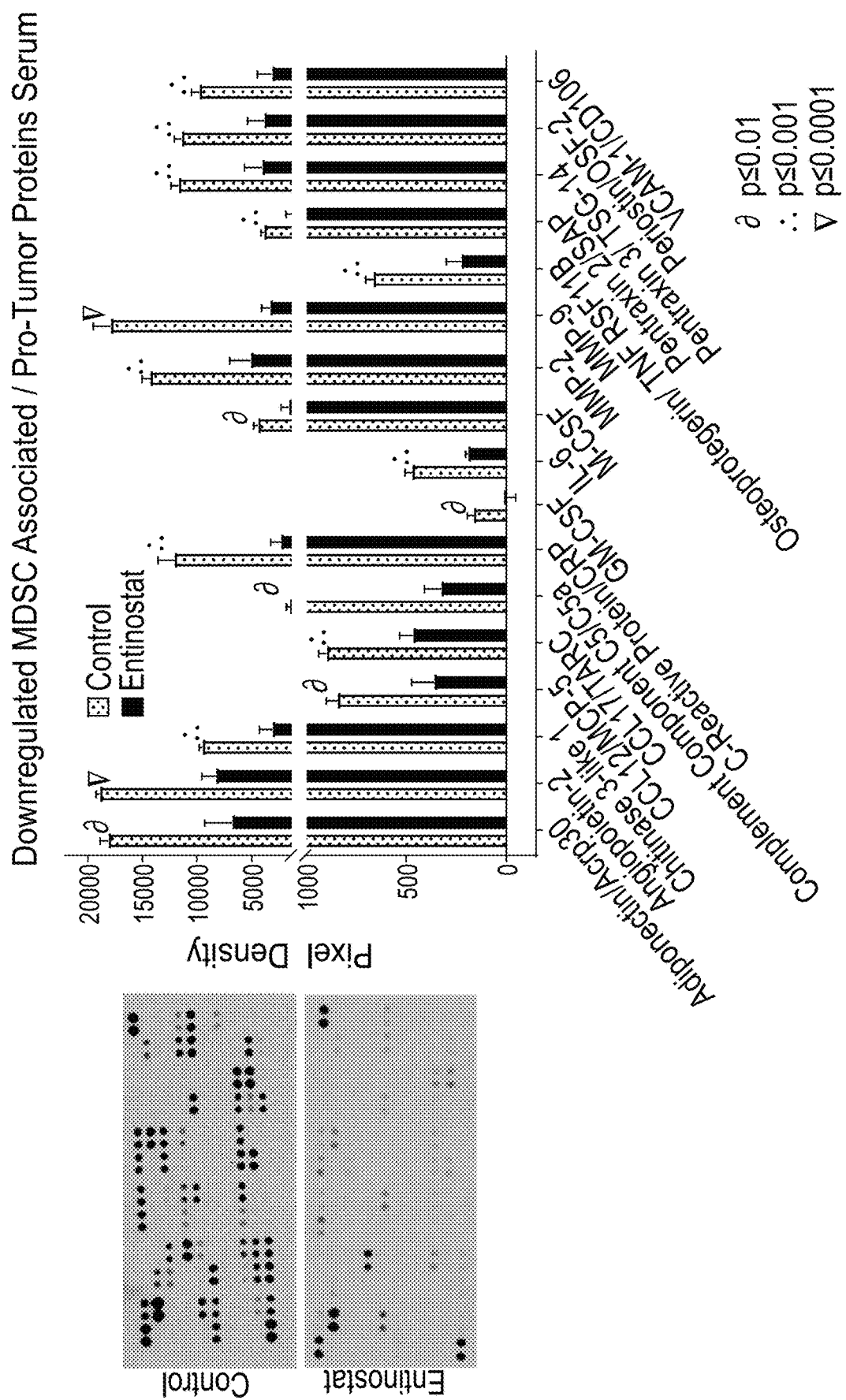
Figure 5E:
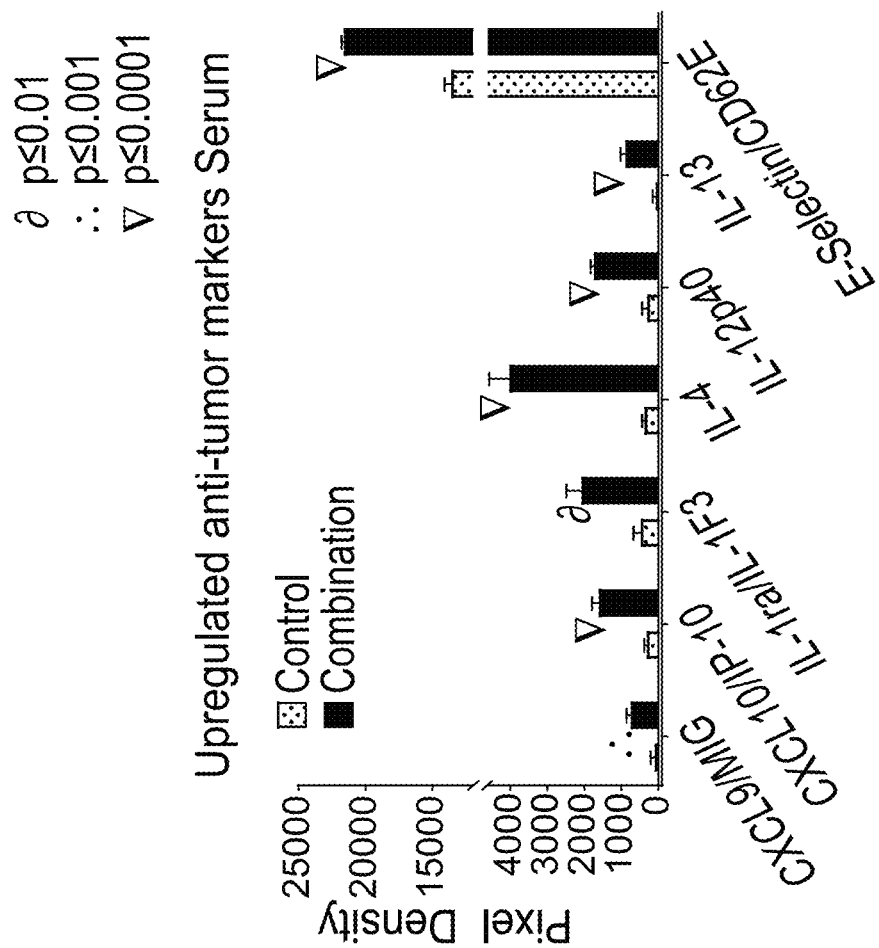
Figure 5E:
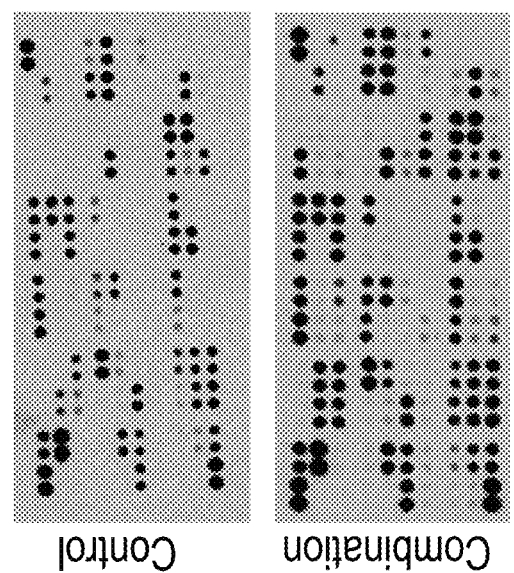
Figure 6:
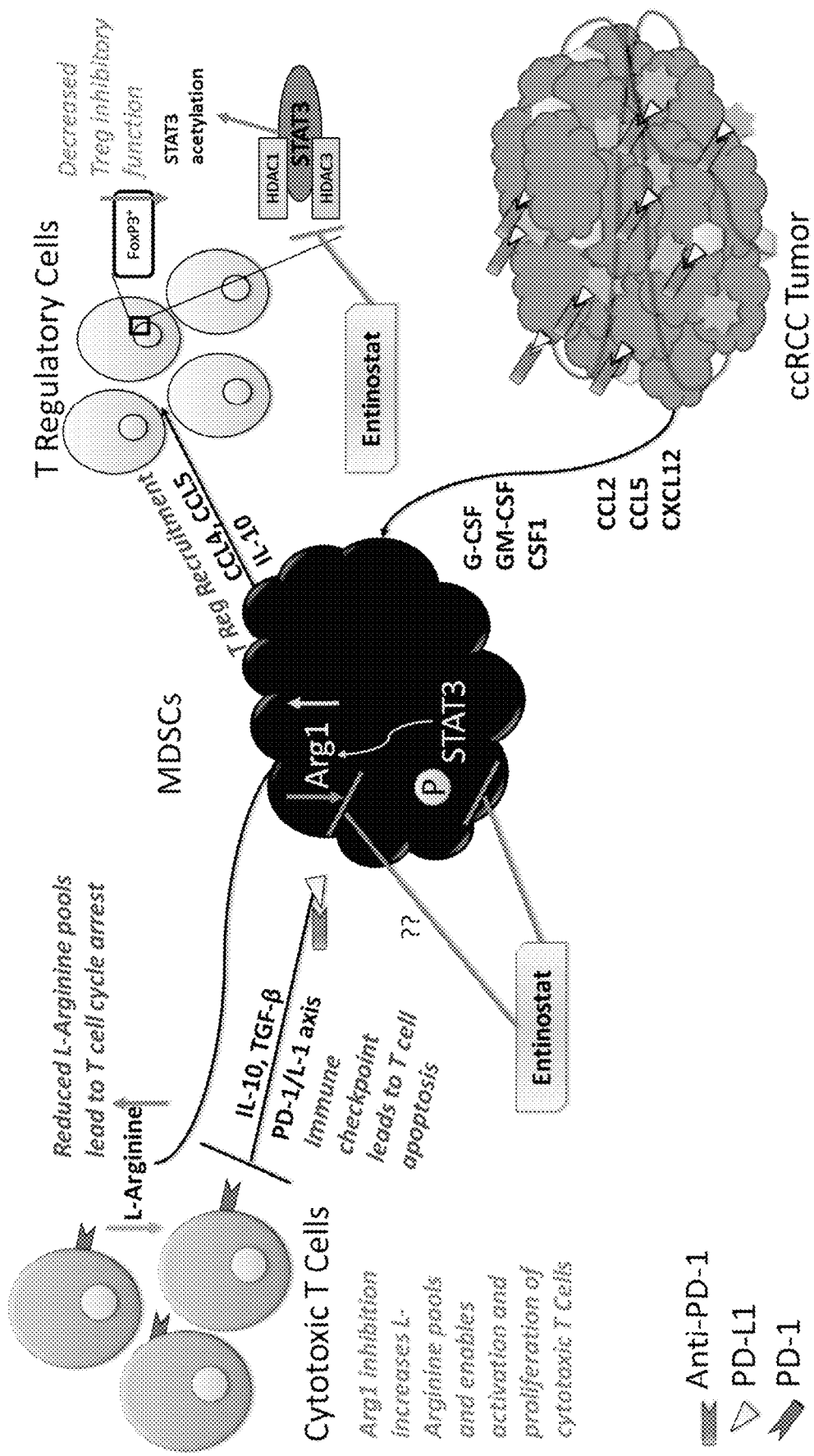
FIG. 6 depicts a schematic representation of entinostat alterations of the innate and adaptive immune responders to ccRCC. Included are models of how entinostat inhibits T regulatory cell activity. Additionally shown is the postulated mechanisms by which entinostat inhibits MDSC function via downregulating Arginasel and thus freeing pools of L-Arginine, which are required for cytotoxic T cell activation.

To examine the role of entinostat on the TME immune status, tumor samples of the control and entinostat treated cohorts were subjected to a proteome profiler analysis (Ary028), which provided a readout of 111 chemokines and cytokines including differing profiles of the control and entinostat treated cohorts. Within this pool, a significant reduction in MDSC associated trafficking/accumulation (CCL2: p≤0.0001, VCAM-1/CD106: p≤0.0001/Angiopoietin-2: p≤0.001), expansion/activation cytokines (G-CSF: p≤0.001, GM-CSF: p≤0.01, IL-1β: p≤0.001, & IL-10: p≤0.0001) in the TME was observed. A significant upregulation of anti-tumor chemokines and cytokines was also noted, which contribute to anti-tumor immune memory (CXCL10/IP-10: p≤0.01), T cell attraction (E-selectin: p≤0.0001), pro-MDSC inhibition (IL-1ra: p≤0.01) and innate anti-tumor response (IL-4: p≤0.001 & IL-12p40: p≤0.01) (FIG. 5A). These results suggest that entinostat treatment is sufficient to alter the immune status of the TME towards an anti-tumor status, which may prime the TME to better respond to immunotherapeutic interventions, such as anti-PD-1 treatment. For these data on entinostat treatment priming the host immune system for response to immunotherapeutic treatments to be translatable into the clinic, serum samples from the control and entinostat treated mice were subjected to the same Ary028 proteome profiler. Significant decreases in multiple, circulating pro-tumor associated chemokines and cytokines were observed between the control and entinostat treated cohorts. Among these were MDSC expansion regulator, adiponectin (p≤0.01); pro-tumor chemoattractant, angiopoietin-2 (p≤0.001); inflammation promoting chitinase 3-like 1 (p≤0.001), CCL12 (p≤0.01), complement component C5 (p≤0.001), c-reactive protein (p≤0.001), IL-6 (p≤0.0001), pentraxins 2/3 (p≤0.01) & periostin (p≤0.001); T regulatory cell chemokine, CCL17 (p≤0.001), MDSC chemoattractants M-CSF (p≤0.01) and GM-CSF (p≤0.01); EMT/invasion matrix-metalloproteinases, MMP-2 (p≤0.001) & MMP-9 (p≤0.0001); CCL2 (p≤0.01)—MDSC attractant—inducing osteoprotegerin (p≤0.001); and leukocyte attractant VCAM (p≤0.001).

While an upregulation of anti-tumor cytokines/chemokines was note observed in the entinostat treated group, a significant upregulation of multiple cytokines/chemokines was seen in the combination cohort, suggesting that anti-PD-1 immunotherapy and entinostat work together to enhance the host immune system for improved immunotherapeutic responses. Also observed were increases in the following anti-tumor related cytokines/chemokines: T cell attractants & anti-endothelial markers (CXCL9 (p≤0.001), CXCL10 (p≤0.0001)), tumor proliferation inhibitory cytokines (IL-4 (p≤0.0001) & IL-13 (p≤0.0001)), T cell chemoattractant (E-selectin (p≤0.0001)), and anti-tumor marker (IL-12p40 (p≤0.0001)). Taken together, these results suggest that entinostat treatment alters the host environment and the TME in a manner that allows for enhancement of anti-PD-1 immunotherapy treatment.

The above results show that treatment with entinostat modulates the function of myeloid derived suppressor cells, thus modulating the TME. The modulation leads to an amplified immune response and augmented anti-tumor responses to immunotherapeutic treatment. Moreover, a synergistic anti-tumor effect was observed when combining entinostat with anti-PD-1 immunotherapy in a mouse model of clear cell renal cell carcinoma. In addition to delayed tumor growth, it is shown that entinostat and anti-PD-1 immunotherapy work synergistically to prolong survival in the ccRCC model.

In accord with previous results, entinostat treatment showed a direct effect on the presence and functional status of T regulatory cells. Combination treatment reduced tumor associated FoxP3+ cells, which had been slightly elevated with anti-PD-1 treatment and significantly reduced the presence of FoxP3 protein in the cells suggesting synergistic anti-tumor activity. T regulatory inhibition due to entinostat treatment was accompanied by increased CD8+ infiltration into the TME and a subsequent increase in the CD8+ to TReg ratio. These findings support the notion that entinostat in combination with immunotherapy treatment, rather than being directly cytotoxic to the tumor, has significant immunomodulatory activity.

Recent analysis of a phase II clinical in breast cancer patients showed a decrease in both monocytic and granulocytic MDSCs in the tumor microenvironment. In experimental conditions, a significant increase in both monocytic and granulocytic subsets of the MDSC population was seen. These data taken together suggest that the specific tumor microenvironment may play a role in different observations seen across tumor types.

indol-3-yl)ethyl)(2-hydroxyethyl)amino)methyl)phenyl)-N-hydroxyacrylamide), butyrate, valproic acid (VPA), Belinostat ((2E)-N-Hydroxy-3-[3-(phenylsulfamoyl)phenyl]prop-2-enamide), Panobinostat ((2E)-N-hydroxy-3-[4-({[2-(2-methyl-1H-indol-3-yl)ethyl]amino}methyl)phenyl]acrylamide), pyroxamide, SK-7041 (4-(dimethylamino)-N-[[4-[(E)-3-(hydroxyamino)-3-oxoprop-1-enyl]phenyl]methyl]benzamide), SK-7068 (N-[[4-[3-(hydroxyamino)-3-oxoprop-1-enyl]phenyl]methyl]-4-pyrrolidin-1-ylbenzamide), Trapoxin A (Cyclo((S)-gamma-oxo-L-alpha-aminooxiraneoctanoyl-L-phenylalanyl-L-phenylalanyl-D-2-piperidinecarbonyl)), cyclic tetrapeptide hydroxamic acid analogues (CHAPs), depudecin (4,5:8,9-Dianhydro-1,2,6,7,11-pentadeoxy-D-threo-D-ido-undeca-1,6-dienitol), Mocetinostat (N-(2-Aminophenyl)-4-[[(4-pyridin-3-ylpyrimidin-2-yl)amino]methyl] benzamide) and combinations thereof.

---

---

What is claimed is:

1. A method of suppressing regulatory T cells in an individual in need, the method comprising administering a composition comprising a class I histone deacetylase (HDAC) inhibitor and a composition comprising a programmed cell death protein 1 (PD-1) inhibitor to the individual.

2. The method of claim 1, wherein the class I HDAC inhibitor is selected from the group consisting of entinostat (Pyridin-3-ylmethyl N-[[4-[(2-aminophenyl)carbamoyl]phenyl]methyl]carbamate), vorinostat (N-Hydroxy-N'-phenyloctanediamide) and Trichostatin A (TSA) ((2E,4E,6R)-7-[4-(Dimethylamino)phenyl]-N-hydroxy-4,6-dimethyl-7-oxo-2,4-heptadienamide), Dacinostat ((E)-3-(4-(((2-(1H-

3. The method of claim 1, wherein the class I HDAC inhibitor composition comprises from about 0.5 μM to about 2 μM of the class I HDAC inhibitor.

4. The method of claim 1, wherein the class I HDAC inhibitor is entinostat.

5. The method of claim 4, wherein the class I HDAC inhibitor composition comprises about 0.5 μM entinostat.

6. The method of claim 1, wherein the PD-1 inhibitor is selected from the group consisting of nivolumab, pembrolizumab and combinations thereof.

7. The method of claim 1, wherein the PD-1 inhibitor is nivolumab.

8. The method of claim 7, wherein the PD-1 inhibitor composition comprises about 1.0 μM nivolulmab.

9. The method of claim 6, wherein the PD-1 inhibitor composition is administered by infusion.

10. The method of claim 1, wherein at least one of the class I HDAC inhibitor composition and the PD-1 inhibitor composition further comprises a pharmaceutically acceptable carrier.

11. The method of claim 1, wherein the individual has renal cell carcinoma.

12. The method of claim 4, wherein the entinostat is administered at a dose of 5 mg.

13. The method of claim 12, wherein the entinostat is administered weekly.

14. The method of claim 13, wherein the class I HDAC inhibitor composition and the PD-1 inhibitor composition are administered at different time intervals.

15. A method of treating renal cell carcinoma, the method comprising administering a class I HDAC inhibitor composition comprising entinostat and a programmed cell death protein 1 (PD-1) inhibitor composition comprising a programmed cell death protein 1 (PD-1) inhibitor.

16. The method of claim 15, wherein the entinostat is administered at a dose of 5 mg.

17. The method of claim 16, wherein the entinostat is administered weekly.

18. The method of claim 17, wherein the class I HDAC inhibitor composition and the PD-1 inhibitor composition are administered at different time intervals.

19. The method of claim 18, wherein the PD-1 inhibitor is selected from the group consisting of nivolumab, pembrolizumab and combinations thereof.

20. The method of claim 19, wherein the PD-1 inhibitor composition is administered by infusion.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
aactttggca ttgtggaagg                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
gtgaagaacc cacggtctgt                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ctggttgtca ggggagtgtt                                              20